US006524793B1

(12) United States Patent
Chandler et al.

(10) Patent No.: US 6,524,793 B1
(45) Date of Patent: Feb. 25, 2003

(54) MULTIPLEXED ANALYSIS OF CLINICAL SPECIMENS APPARATUS AND METHOD

(75) Inventors: Van S. Chandler, Dallas, TX (US); R. Jerrold Fulton, Cedar Hill, TX (US); Mark B. Chandler, Austin, TX (US)

(73) Assignee: Luminex Corporation, Austin, TX (US)

( * ) Notice: Subject to any disclaimer, the term of this patent is extended or adjusted under 35 U.S.C. 154(b) by 0 days.

(21) Appl. No.: 09/335,719

(22) Filed: Jun. 18, 1999

Related U.S. Application Data

(63) Continuation of application No. 08/540,814, filed on Oct. 11, 1995, now Pat. No. 5,981,180, which is a continuation of application No. 08/542,401, filed on Oct. 11, 1995, now Pat. No. 5,736,330.

(51) Int. Cl.[7] .......................... G01N 33/53; C12Q 1/68
(52) U.S. Cl. ...................... 435/6; 435/7.1; 435/7.7; 435/7.72; 435/7.2; 435/7.71; 435/7.91; 435/7.92; 435/973; 436/63; 436/536; 436/534; 436/523
(58) Field of Search .............................. 435/6, 7.1, 7.7, 435/7.72, 7.2, 7.71, 7.91, 7.92, 973; 436/63, 536, 534

(56) References Cited

U.S. PATENT DOCUMENTS

| 3,952,091 A | 4/1976 | Grunberg et al. ............. 424/1.5 |
| 3,959,650 A | 5/1976 | Lukens, Jr. ................. 250/303 |
| 3,985,867 A | 10/1976 | Redshaw ..................... 424/1.5 |

(List continued on next page.)

FOREIGN PATENT DOCUMENTS

| CA | 1248873 | 1/1989 |
| EP | 02001132 A | 4/1986 |
| EP | 0382433 A2 | 2/1990 |
| EP | 0633462 A2 | 6/1994 |
| WO | WO 87/06621 | 11/1987 |
| WO | WO 89/11101 | 11/1989 |
| WO | WO 92/17853 | 10/1992 |
| WO | WO 93/02360 | 2/1993 |

OTHER PUBLICATIONS

Mack J. Fulwyler and Thomas M. McHugh, "Flow Microsphere Immunoassay for the Quantitative and Simultaneous Detection of Multiple Soluble Analytes", *Methods in Cell Biology*, vol. 33, pp. 613–619.

Bottema et al., "PCR Amplification of Specific Alleles: Rapid Detection of Known Mutations and Polymorphisms," Mutation Research, 288, 93–102 (1993).

Cantarero et al., "The Adsorptive Characteristics of Proteins for Polystyrene and Their Significance in Solid–Phase Immunoassays," Analytical Biochemistry, 105, 375–382 (1980).

(List continued on next page.)

*Primary Examiner*—Christopher L. Chin
*Assistant Examiner*—Pensee T. Do
(74) *Attorney, Agent, or Firm*—Gilberto M. Villacorta; Serge Sira; Katten Muchin Zavis Rosenman

(57) ABSTRACT

A method for the multiplexed diagnostic and genetic analysis of enzymes, DNA fragments, antibodies, and other biomolecules comprises the steps of constructing an appropriately labeled beadset, exposing the beadset to a clinical sample, and analyzing the combined sample/beadset by flow cytometry. Flow cytometric measurements are used to classify, in real-time, beads within an exposed beadset and textual explanations, based on the accumulated data obtained during real-time analysis, are generated for the user. The inventive technology enables the simultaneous, and automated, detection and interpretation of multiple biomolecules or DNA sequences in real-time while also reducing the cost of performing diagnostic and genetic assays.

23 Claims, 20 Drawing Sheets

U.S. PATENT DOCUMENTS

| | | | |
|---|---|---|---|
| 4,010,250 A | 3/1977 | Parikh et al. ................... 424/1 |
| 4,018,884 A | 4/1977 | Cleeland, Jr. et al. .......... 424/7 |
| 4,028,056 A | 6/1977 | Snyder et al. ............. 23/230 B |
| 4,075,462 A | 2/1978 | Rowe .......................... 235/92 |
| 4,088,746 A | 5/1978 | Blakemore et al. ............ 424/1 |
| 4,090,850 A | 5/1978 | Chen et al. ................... 23/259 |
| 4,108,972 A | 8/1978 | Dreyer .......................... 424/1 |
| 4,108,974 A | 8/1978 | Wegfahrt et al. .............. 424/1 |
| 4,113,433 A | 9/1978 | Khare ....................... 23/230.6 |
| 4,115,535 A | 9/1978 | Giaever ......................... 424/1 |
| 4,115,536 A | 9/1978 | Rothman et al. .............. 424/1 |
| 4,166,102 A | 8/1979 | Johnson ......................... 424/1 |
| 4,166,105 A | 8/1979 | Hirschfeld ..................... 424/8 |
| 4,169,137 A | 9/1979 | Hirschfeld et al. ............ 424/8 |
| 4,177,253 A | 12/1979 | Davies et al. .................. 424/1 |
| 4,182,750 A | 1/1980 | Sullivan et al. ................ 424/1 |
| 4,184,849 A | 1/1980 | Cambiaso et al. ........ 23/230 B |
| 4,201,763 A | 5/1980 | Monthony et al. ............. 424/8 |
| 4,217,339 A | 8/1980 | Bohn et al. ................... 424/12 |
| 4,219,335 A | 8/1980 | Ebersole ................... 23/230 B |
| 4,225,783 A | 9/1980 | Palin et al. ................. 250/302 |
| 4,231,750 A | 11/1980 | Dowben et al. ......... 23/230 B |
| 4,244,940 A | 1/1981 | Jeong et al. .................... 424/1 |
| 4,254,096 A | 3/1981 | Monthony et al. ............. 424/8 |
| 4,259,313 A | 3/1981 | Frank et al. .................... 424/8 |
| 4,278,653 A | 7/1981 | Harris et al. ................... 424/1 |
| 4,283,382 A | 8/1981 | Frank et al. .................... 424/8 |
| 4,302,536 A | 11/1981 | Longenecker ................. 435/7 |
| 4,317,810 A | 3/1982 | Halbert et al. ............... 424/12 |
| 4,340,564 A | 7/1982 | Harte et al. .................. 422/56 |
| 4,341,957 A | 7/1982 | Wieder .................... 250/461.2 |
| 4,342,739 A | 8/1982 | Kakimi et al. ................. 424/1 |
| 4,499,052 A | 2/1985 | Fulwyler ..................... 422/52 |
| 4,661,913 A | 4/1987 | Wu et al. .................... 364/500 |
| 4,665,020 A | 5/1987 | Saunders ........................ 435/7 |
| 4,673,288 A | 6/1987 | Thomas et al. ............... 356/72 |
| 4,676,640 A | 6/1987 | Briggs ........................ 356/317 |
| 4,710,021 A | 12/1987 | von Behrens ................ 356/72 |
| 4,713,348 A | 12/1987 | Ullman ....................... 436/501 |
| 4,767,205 A | 8/1988 | Schwartz et al. ............. 356/71 |
| 4,778,593 A | 10/1988 | Yamashita et al. ........... 209/3.1 |
| 4,857,451 A | 8/1989 | Schwartz ........................ 435/7 |
| 4,868,104 A | 9/1989 | Kurn et al. ..................... 435/6 |
| 4,884,886 A | 12/1989 | Salzman et al. ............ 356/367 |
| 4,887,721 A | 12/1989 | Martin et al. ............... 209/579 |
| 4,905,169 A | 2/1990 | Buican et al. ............... 364/525 |
| 4,918,004 A | 4/1990 | Schwartz ........................ 435/7 |
| 4,987,539 A | 1/1991 | Moore et al. .......... 364/413.08 |
| 5,028,545 A | 7/1991 | Soini ........................... 436/501 |
| 5,093,234 A | 3/1992 | Schwartz .................... 435/7.21 |
| 5,104,791 A | 4/1992 | Abbott et al. ................... 435/6 |
| 5,107,422 A | 4/1992 | Kamentsky et al. ... 364/413.08 |
| 5,127,730 A | 7/1992 | Brelje et al. ................. 356/318 |
| 5,149,661 A | 9/1992 | Gjerde et al. ............... 436/178 |
| 5,150,313 A | 9/1992 | van den Engh et al. .... 364/569 |
| 5,156,810 A | 10/1992 | Ribi ........................ 422/82.01 |
| 5,199,576 A | 4/1993 | Corio et al. ................. 209/564 |
| 5,204,884 A | 4/1993 | Leary et al. ................... 377/10 |
| 5,219,763 A | 6/1993 | Van Hoegaerden ......... 436/523 |
| 5,224,058 A | 6/1993 | Michaels et al. ............ 364/554 |
| 5,273,881 A | 12/1993 | Sena et al. ...................... 425/6 |
| 5,281,517 A | 1/1994 | Bacus et al. .................... 435/6 |
| 5,286,452 A | 2/1994 | Hansen ........................ 422/73 |
| 5,290,707 A | 3/1994 | Wood ........................ 436/523 |
| 5,319,079 A | 6/1994 | Reddy et al. ............. 536/25.32 |
| 5,326,692 A | 7/1994 | Brinkley et al. ............... 435/6 |
| 5,367,474 A | 11/1994 | Auer et al. .................. 364/555 |
| 5,380,663 A | 1/1995 | Schwartz et al. ............. 436/10 |
| 5,385,822 A | 1/1995 | Melnicoff et al. ............. 435/5 |
| 5,393,673 A | 2/1995 | Gjerde ....................... 436/171 |
| 5,401,847 A | 3/1995 | Glazer et al. ................ 546/107 |
| 5,403,711 A | 4/1995 | Walder et al. .................. 435/6 |
| 5,405,784 A | 4/1995 | Van Hoegaerden ......... 436/523 |
| 5,408,307 A | 4/1995 | Yamamoto et al. ............ 356/73 |
| 5,413,907 A | 5/1995 | Worton et al. .................. 435/6 |
| 5,429,923 A | 7/1995 | Seidman et al. ............... 435/6 |

OTHER PUBLICATIONS

Colvin et al., "The Covalent Binding of Enzymes and Immunoglobulins to Hydrophilic Microspheres" in Microspheres: Medical and Biological Applications, 1–13, CRC, Boca Raton, FL, 1988.

Fisher, "The Use of Multiple Measurements in Taxonomic Problems," Annals of Eugenics, 7, 179–188 (1936).

Fulwyler et al., "Flow Microsphere Immunoassay for the Quantitative and Simultaneous Detection of Multiple Soluble Analytes," Methods in Cell Biology, 33, 613–629 (1990).

Goss et al., "Major Histocompatibility Complex–specific Prolongation of Murine Skin and Cardiac Allograft Survival after In Vivo Depletion of $V\mu^+T$ Cells," The Journal of Experimental Medicine, 177, 35–44 (1993).

Horan et al., "Fluid Phase Particle Fluorescence Analysis: Rheumatoid Factor Specificity Evaluated by Laser Flow Cytophotometry" in Immunoassays in the Clinical Laboratory, 185–198 (Liss 1979).

Illum et al., "Attachment of Monoclonal Antibodies to Microspheres," Methods in Enzymology, 112, 67–84 (1985).

Lindemo et al., "Immunometric Assay by Flow Cytometry Using Mixtures of Two Particle Types of Different Affinity," Journal of Immunological Methods, 126, 183–189 (1990).

McHugh, "Flow Microsphere Immunoassay for the Quantitative and Simultaneous Detection of Multiple Soluble Analytes," in Methods in Cell Biology, 42, Part B, 575–595 (Academic Press 1994).

McHugh et al., "Microsphere–Based Fluorescence Immunoassays Using Flow Cytometry Instrumentation," in Clinical Flow Cytometry Ed. K. D. Bauer, et al., Williams and Williams, Baltimore, MD, 1993, 535–544.

McHugh, "Flow Cytometry and theApplication of Microsphere–Based Fluorescence Immunoassays," Immunochemica, 5, 1–6 (1991).

Saiki et al., "Genetic Analysis of Amplified DNA with Immobilized Sequence–Specific Oligonucleotide Probes," Proceedings of the National Academy of Sciences of the United States of America, 86, 6230–6234 (1989).

Vener et al., "A Novel Approach to Nonradioactive Hybridization Assay of Nucleic Acids Using Stained Latex Particles," Analytical Biochemistry, 198, 308–311 (1991).

Vlieger et al., "Quantitation of Polymerase Chain Reaction Products by Hybridization–Based Assays with Fluorescent, Colorimetric, or Chemiluminescent Detection," Analytical Biochemistry, 205, 1–7 (1992).

Wilson et al., "A New Microsphere–Based Immunofluorescence Assay Using Flow Cytometry," Journal of Immunological Methods, 107, 225–230 (1988).

| ANALYTE | $C_1$: SIDE LIGHT SCATTER | $C_2$: FORWARD LIGHT SCATTER | $C_3$: ORANGE FLUORESCENCE | $C_4$: RED FLUORESCENCE | $F_1$: GREEN FLUORESCENCE |
|---|---|---|---|---|---|
| 1 | = 560<br>= 5.1 | | = 0 | = 0 | = 170<br>= 1.3 |
| 2 | = 579<br>= 5.1 | | = 48<br>= 0.69 | = 368<br>= 1.92 | = 170<br>= 1.3 |
| 3 | = 519<br>= 4.56 | | = 98<br>= 0.99 | = 550<br>= 2.35 | = 170<br>= 1.3 |
| 4 | = 519<br>= 4.56 | | = 0 | = 527<br>= 2.30 | = 170<br>= 1.3 |

* NOT USED IN ILLUSTRATIVE EXAMPLE

FIG. 5

| ASSAY NAME | SUBSET TOKEN | SUBSET NAME | $F_1$'s BASE VALUE | $F_1$'s STANDARD DEVIATION | TEST TYPE TOKEN |
|---|---|---|---|---|---|
| test_assay | 46 | KRAS CODON 46 WILDTYPE | 170 | 1.3 | 0 |
| test_assay | 21 | KRAS CODON 21 MUTANT | 170 | 1.3 | 0 |
| test_assay | 50 | KRAS CODON 50 MUTANT | 170 | 1.3 | 0 |
| test_assay | 5 | KRAS CODON 5 MUTANT | 170 | 1.3 | 0 |

FIG. 6

| ASSAY NAME | ROW ID | PARAMETER | LOW VALUE | HIGH VALUE | TRUE ROW ID | FALSE ROW ID | TRUE TOKEN | FALSE TOKEN |
|---|---|---|---|---|---|---|---|---|
| test_assay | 0 | $C_1$ | 500 | 620 | 1 | 0 | 0 | 0 |
| test_assay | 1 | $C_4$ | 0 | 514 | 2 | 3 | 0 | 0 |
| test_assay | 2 | $C_4$ | 0 | 200 | 0 | 0 | 50 | 5 |
| test_assay | 3 | $C_3$ | 0 | 98 | 0 | 0 | 46 | 21 |

FIG. 7

| ASSAY NAME | SUBSET TOKEN | COUNT | SUM | OVER COUNT | UNDER COUNT |
|---|---|---|---|---|---|
| test_assay | 46 | 1,000 | 71,111 | | |
| test_assay | 21 | 1,000 | 90,000 | | |
| test_assay | 50 | 1,000 | 1,700,000 | | |
| test_assay | 5 | 1,000 | 70,000 | | |

\* NOT USED IN ILLUSTRATIVE EXAMPLE

FIG. 10

| ASSAY NAME | SUBSET TOKEN | OUTCOME TOKEN | TEST-TYPE TOKEN | LOW VALUE | HIGH VALUE | INTERPRETATION |
|---|---|---|---|---|---|---|
| test_assay | 5 | 1 | 1 | 10 | 667 | IDENTICAL COMPLEMENTARY STRAND |
| test_assay | 5 | 2 | 1 | 668 | 970 | SIMILAR OLIGO |
| test_assay | 5 | 3 | 1 | 971 | 2,000 | NOT FOUND IN SAMPLE |
| test_assay | 21 | 1 | 1 | 10 | 667 | IDENTICAL COMPLEMENTARY STRAND |
| test_assay | 21 | 2 | 1 | 668 | 970 | SIMILAR OLIGO |
| test_assay | 21 | 3 | 1 | 971 | 2,000 | NOT FOUND IN SAMPLE |
| test_assay | 50 | 1 | 1 | 10 | 667 | IDENTICAL COMPLEMENTARY STRAND |
| test_assay | 50 | 2 | 1 | 668 | 970 | SIMILAR OLIGO |
| test_assay | 50 | 3 | 1 | 971 | 2,000 | NOT FOUND IN SAMPLE |
| test_assay | 46 | 1 | 1 | 10 | 667 | IDENTICAL COMPLEMENTARY STRAND |
| test_assay | 46 | 2 | 1 | 558 | 970 | SIMILAR OLIGO |
| test_assay | 46 | 3 | 1 | 971 | 2,000 | NOT FOUND IN SAMPLE |

FIG. 11

| ANTIGEN | MICROSPHERE INDETIFIED VIA DYE COLOR | ANTIGEN-MICROSPHERE COMPLEX | FLUORESCENT ANTIBODY ($F_m$) | SUBSET TOKEN |
|---|---|---|---|---|
| LH | 1 mCRIMSON BEADS | LH—CRIMSON BEADS | anti-LH | 18 |
| TSH | 1 mDARK RED BEADS | TSH—DARK RED BEADS | anti-TSH | 45 |
| IgA | 3 mCLEAR BEADS | IgA—CLEAR BEADS | anti-Ig | 50 |

FIG. 13a

| BEAD SUBSET DYE COLOR (TOKEN) | $C_1$ MEAN SIDE LIGHT SCATTER | $C_2$ MEAN ORANGE FLUORESCENCE | $C_3$ MEAN RED FLUORESCENCE | $F_m$ MEAN GREEN FLUORESCENCE |
|---|---|---|---|---|
| CRIMSON (18) | 38.46 | 1.71 | 30.69 | 9.15 |
| DARK RED (45) | 40.37 | 0.00 | 88.62 | 5.44 |
| CLEAR (50) | 167 | 0.00 | 0.00 | 7.83 |

FIG. 13b

| ROW ID | PARAMETER | LOW VALUE | HIGH VALUE | TRUE NODE | FALSE NODE | TRUE TOKEN | FALSE TOKEN |
|---|---|---|---|---|---|---|---|
| 0 | $C_3$ | 0 | 5 | 3 | 1 | 0 | 0 |
| 1 | $C_1$ | 400 | 420 | 2 | 0 | 0 | 0 |
| 2 | $C_3$ | 0 | 454 | 0 | 0 | 18 | 45 |
| 3 | $C_1$ | 560 | 580 | 0 | 0 | 50 | 0 |

FIG. 13c

| SUBSET TOKEN | OUTCOME ID | TEST-TYPE TOKEN | LOW VALUE | HIGH VALUE | INTERPRETATION |
|---|---|---|---|---|---|
| 18 | 1 | 1 | 289.35 | - | Anti-LH FOUND |
| 18 | 2 | 1 | - | 289.35 | Anti-LH NOT FOUND |
| 45 | 1 | 1 | 172.03 | - | Anti-TSH FOUND |
| 45 | 2 | 1 | - | 172.03 | Anti-TSH NOT FOUND |
| 50 | 1 | 1 | 247.61 | - | Anti-IgA FOUND |
| 50 | 2 | 1 | - | 247.61 | Anti-IgA NOT FOUND |

FIG. 13d

| SAMPLE | ANTIBODY PRESENT | MEASURED $F_m$ SUBSET 18 | MEASURED $F_m$ SUBSET 45 | MEASURED $F_m$ SUBSET 50 |
|---|---|---|---|---|
| 1 | Anti—IgA | 70 | 10 | 6049 |
| 2 | anti—LH | 132 | 442 | 180 |
| 3 | anti—TSH | 2124 | 108 | 182 |
| 4 | anti—IgA + anti—TSH | 2152 | 115 | 5917 |

FIG. 13e

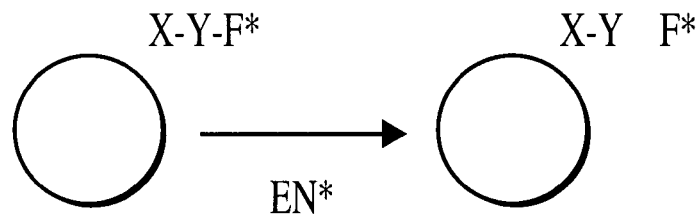
FIG. 15e
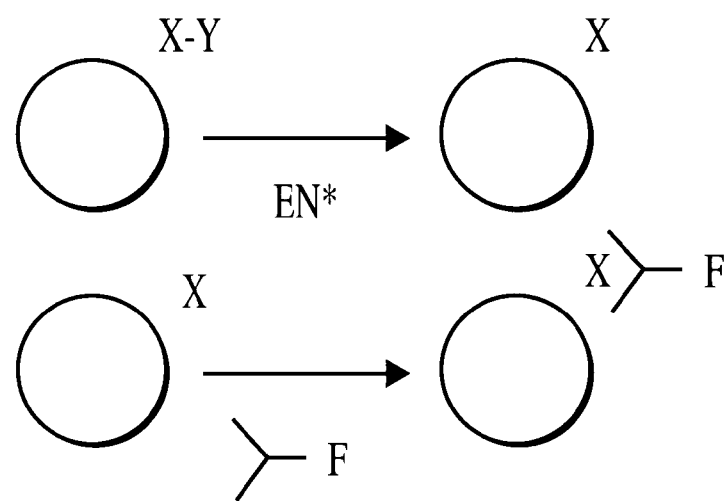
FIG. 15f

MULTIPLEXED ANALYSIS OF CLINICAL SPECIMENS APPARATUS AND METHOD

RELATED APPLICATIONS

This application is a continuation of U.S. application Ser. No. 08/540,814, filed Oct. 11, 1995, now U.S. Pat. No. 5,981,180, issued Nov. 9, 1999. This application is also related to U.S. application Ser. No. 08/542,401, filed Oct. 11, 1995, now U.S. Pat. No. 5,736,330, issued Apr. 7, 1998, those patents are specifically herein incorporated by reference.

1. REFERENCES

Commonly owned, and co-pending patent application, entitled "Methods and Compositions for Flow Cytometric Determination of DNA Sequences by R. Jerrold Fulton, filed on Oct. 11, 1995, is hereby incorporated in its entirety by reference.

Microfiche appendix A contains a listing of selected Visual Basic and C programming source code in accordance with the inventive multiplexed assay method. Microfiche appendix A, comprising 1 sheet having a total of 58 frames, contains material which is subject to copyright protection. The copyright owner has no objection to the facsimile reproduction by anyone of the patent disclosure, as it appears in the Patent and Trademark Office patent files or records, but otherwise reserves all copyright rights whatsoever.

2. FIELD OF THE INVENTION

The invention relates generally to laboratory diagnostic and genetic analysis and, more particularly, to a flow cytometric method for the simultaneous and multiplexed diagnostic and genetic analysis of clinical specimens.

3. BACKGROUND OF THE INVENTION

Analysis of clinical specimens is important in science and medicine. A wide variety of assays to determine qualitative and/or quantitative characteristics of a specimen are known in the art. Detection of multiple analytes, or separately identifiable characteristics of one or more analytes, through single-step assay processes are presently not possible or, to the extent possible, have provided only very limited capability and have not yielded satisfactory results. Some of the reasons for these disappointing results include the extended times typically required to enable the detection and classification of multiple analytes, the inherent limitations of known reagents, the low sensitivities achievable in prior art assays which often lead to significant analytical errors and the unwieldy collection, classification, and analysis of prior art algorithms vis a vis the large amounts of data obtained and the subsequent computational requirements to analyze that data.

Clearly, it would be an improvement in the art to have adequate apparatus and methods for reliably performing real-time multiple determinations, substantially simultaneously, through a single or limited step assay process. A capability to perform simultaneous, multiple determinations in a single assay process is known as "multiplexing" and a process to implement such a capability is a "multiplexed assay."

3.1 Flow Cytometry

One well known prior art technique used in assay procedures for which a multiplexed assay capability would be particularly advantageous is flow cytometry. Flow cytometry is an optical technique that analyzes particular particles in a fluid mixture based on the particles' optical characteristics using an instrument known as a flow cytometer. Background information on flow cytometry may be found in Shapiro, "Practical Flow Cytometry," Third Ed. (Alan R. Liss, Inc. 1995); and Melamed et al., "Flow Cytometry and Sorting," Second Ed. (Wiley-Liss 1990), which are incorporated herein by reference.

Flow cytometers hydrodynamically focus a fluid suspension of particles into a thin stream so that the particles flow down the stream in substantially single file and pass through an examination zone. A focused light beam, such as a laser beam illuminates the particles as they flow through the examination zone. Optical detectors within the flow cytometer measure certain characteristics of the light as it interacts with the particles. Commonly used flow cytometers such as the Becton-Dickinson Immunocytometry Systems "FACSCAN" can measure forward light scatter (generally correlated with the refractive index and size of the particle being illuminated), side light scatter (generally correlated with the particle's size), and particle fluorescence at one or more wavelengths. (Fluorescence is typically imparted by incorporating, or attaching a fluorochrome within the particle.) Flow cytometers and various techniques for their use are described in, generally, in "Practical Flow Cytometry" by Howard M. Shapiro (Alan R. Liss, Inc., 1985) and "Flow Cytometry and Sorting, Second Edition" edited by Melamed et al. (Wiley-Liss, 1990).

One skilled in the art will recognize that one type of "particle" analyzed by a flow cytometer may be man-made microspheres or beads. Microspheres or beads for use in flow cytometry are generally known in the art and may be obtained from manufacturers such as Spherotech, and Molecular Probes.

Although a multiplexed analysis capability theoretically would provide enormous benefits in the art of flow cytometry, very little multiplexing capability has been previously achieved. Prior multiplexed assays have obtained only a limited number of determinations. A review of some of these prior art techniques is provided by McHugh, "Flow Microsphere Immunoassay for the Quantitative and Simultaneous Detection of Multiple Soluble Analytes," in Methods in Cell Biology, 42, Part B, (Academic Press, 1994). For example, McHugh et al., "Microsphere-Based Fluorescence Immunoassays Using Flow Cytometry Instrumentation," in Clinical Flow Cytometry Ed. K. D. Bauer, et al, Williams and Williams, Baltimore, Md., 1993, 535–544, describe an assay where microspheres of different sizes are used as supports and the identification of microspheres associated with different analytes was based on distinguishing a microsphere's size. Other references in this area include Lindmo, et al., "Immunometric Assay by Flow Cytometry Using Mixtures of Two Particle Types of Different Affinity," J. Immun. Meth., 126, 183–189 (1990); McHugh, "Flow Cytometry and the Application of Microsphere-Based Fluorescence Immunoassays," Immunochemica, 5, 116 (1991); Horan et al., "Fluid Phase Particle Fluorescence Analysis: Rheumatoid Factor Specificity Evaluated by Laser Flow Cytophotometry" in Immunoassays in the Clinical Laboratory, 185–198 (Liss 1979); Wilson et al., "A New Microsphere-Based Immunofluorescence Assay Using Flow Cytometry," J. of Immunological Methods, 107, 225–230 (1988); and Fulwyler et al., "Flow Microsphere Immunoassay for the Quantitative and Simultaneous Detection of Multiple Soluble Analytes," Methods in Cell Biology, 33, 613–629 (1990).

The above cited methods have been unsatisfactory as applied to provide a fully multiplexed assay capable of real-time analysis of more than a few different analytes. For example, certain of the assay methods replaced a single ELISA procedure with a flow cytometer-based assay. These methods were based on only a few characteristics of the particles under analysis and enabled simultaneous determination of only a very few analytes in the assay. Also, the analytic determinations made were hampered due to software limitations including the inability to perform real-time processing of the acquired assay data. In summary, although it has been previously hypothesized that flow cytometry may possibly be adapted to operate and provide benefit in a multiple analyte assay process, such an adaptation has not in reality been accomplished.

3.2 Analysis of Genetic Information

The availability of genetic information and association of disease with mutation(s) of critical genes has generated a rich field of clinical analysis. In particular, the use polymerase chain reaction (PCR) and its variants have facilitated genetic analysis. A major advance in this field is described in our co-pending and contemporaneously filed U.S. Application entitled "Methods and Compositions for Flow Cytometric.Determination of DNA Sequences." This co-pending application describes a powerful flow cytometric assay for PCR products, which may be multiplexed in accordance with the present invention. A multiplexed flow cytometric assay for PCR reaction products would provide a significant advantage in the field of genetic analysis.

At least one use of flow cytometry for the assay of a PCR product has been reported but that assay has not been adapted to multiplexing. See Vlieger et al., "Quantitation of Polymerase Chain Reaction Products by Hybridization-Based Assays with Fluorescent Colorimetric, or Chemiluminescent Detection," Anal Biochem, 205, 1–7 (1992). In Vlieger et al. a PCR product was labeled using primers that contained biotinylated nucleotides. Unreacted primers were first removed and the amplified portion annealed with a labeled complementary probe in solution. Beaded microspheres of avidin were then attached to the annealed complementary material. The avidin beads bearing the annealed complementary material were then processed by a flow cytometer. The procedure was limited, inter alia, in that avidin beads having only a single specificity were employed. Further, real-time analysis of the assay's data was not possible.

3.3 Data Manipulation

The large volume of data typically generated during flow cytometric multiple analyte assays, combined with the limited capabilities of prior techniques to collect, sort and analyze such data have provided significant obstacles in achieving a satisfactory multiplexed assay. The computing methods used in prior art flow cytometric analyses have generally been insufficient and unsuited for accurately and timely analyzing large volumes of data such as would be generated by multiplexed assays; particularly when more than two analytes (or properties of a single analyte) are to be simultaneously determined.

The present invention enables the simultaneous determination of multiple distinct analytes to a far greater degree than existing techniques. Further, the invention provides an improved data classification and analysis methodology that enables the meaningful analysis of highly multiplexed assays in real-time. The invention is broadly applicable to multiplexed analysis of a number of analytes in a host of bioassays in which there is currently a need in the art.

4. SUMMARY OF THE INVENTION

The present invention provides improved methods, instrumentation, and products for detecting multiple analytes in a fluid sample by flow cytometric analysis and for analyzing and presenting the data in real-time. An advantage of the invention is that it allows one rapidly and simultaneously to detect a wide variety of analytes of interest in a single assay step.

The invention employs a pool of bead subsets. The individual subsets are prepared so that beads within a subset are relatively homogeneous but differ in at least one distinguishing characteristic from beads in any other subset. Therefore, the subset to which a bead belongs can readily be determined after beads from different subsets are pooled.

In a preferred embodiment, the beads within each subset are uniform with respect to at least three and preferably four known classification parameter values measured with a flow cytometer: e.g., forward light scatter ($C_1$) which generally correlates with size and refractive index; side light scatter ($C_2$) which generally correlates with size; and fluorescent emission in at least one wavelength ($C_3$), and preferably in two wavelengths ($C_3$ and $C_4$), which generally results from the presence of fluorochrome(s) in or on the beads. Because beads from different subsets differ in at least one of the above listed classification parameters, and the classification parameters for each subset are known, a bead's subset identity can be verified during flow cytometric analysis of the pool in a single assay step and in real-time.

Prior to pooling subsets of beads to form a beadset, the beads within each subset can be coupled to a reactant that will specifically react with a given analyte of interest in a fluid sample to be tested. Usually, different subsets will be coupled to different reactants so as to detect different analytes. For example, subset 1 may be labeled so as to detect analyte A (AnA); subset 2 may be labeled so as to detect analyte B (AnB); etc.

At some point prior to assay, the variously labeled subsets are pooled. The pooled beads, or beadset, are then mixed with a fluid sample to test for analytes reactive with the various reactants bound to the beads. The system is designed so that reactions between the reactants on the bead surfaces and the corresponding analytes in the fluid sample will cause changes in the intensity of at least one additional fluorescent signal ($F_m$) emitted from a fluorochrome that fluoresces at a wavelength distinct from the wavelengths of classification parameters $C_3$ or $C_4$. The $F_m$ signal serves as a "measurement signal," that is, it indicates the extent to which the reactant on a given bead has undergone a reaction with its corresponding analyte. The $F_m$ signal may result from the addition to the assay mixture of fluorescently labeled "secondary" reagent that binds to the bead surface at the site where a reactant-analyte reaction has occurred.

When the mixture (pooled beads and fluid sample) is run through a flow cytometer, each bead is individually examined. The classification parameters, e.g., $C_1$, $C_2$, $C_3$, and $C_4$, are measured and used to classify each bead into the subset to which it belongs and, therefore, identify the analyte that the bead is designed to detect. The $F_m$ value of the bead is determined to indicate the concentration of analyte of interest in the fluid sample. Not only are many beads from each subset rapidly evaluated in a single run, multiple subsets are evaluated in a single run. Thus, in a single-pass and in real-time a sample is evaluated for multiple analytes. Measured $F_m$ values for all beads assayed and classified as belonging to a given subset may be averaged or otherwise manipulated statistically to give a single meaningful data point, displayed in histogram format to provide information about the distribution of $F_m$ values within the subset, or analyzed as a function of time to provide information about the rate of a reaction involving that analyte.

In a preferred embodiment, the beads will have two or more fluorochromes incorporated within or on them so that each of the beads in a given subset will possess at least four different classification parameters, e.g., $C_1$, $C_2$, $C_3$, and $C_4$. For example, the beads may be made to contain a red fluorochrome ($C_3$), such as nile red, and bear an orange fluorochrome ($C_4$), such as Cy3 or phycoerythrin. A third fluorochrome, such as fluorescein, may be used as a source of the $C_n$ or $F_m$ signal. As those of skill in the art will recognize, additional fluorochromes may be used to generate additional $C_n$ signals. That is, given suitable fluorochromes and equipment, those of skill in the art may use multiple fluorochromes to measure a variety of $C_n$ or $F_m$ values, thus expanding the multiplexing power of the system even further.

In certain applications designed for more quantitative analysis of analyte concentrations or for kinetic studies, multiple subsets of beads may be coupled to the same reactant but at varying concentrations so as to produce subsets of beads varying in density of bound reactant rather than in the type of reactant. In such an embodiment, the reactant associated with classification parameter $C_4$, for example, may be incorporated directly into the reactive reagent that is coupled to the beads, thereby allowing $C_4$ conveniently to serve as an indicator of density of reactant on the bead surface as well as an indicator of reactant identity.

To prepare subsets varying in reactant density one may, for example, select, isolate, or prepare a starting panel of different subsets of beads, each subset differing from the other subsets in one or more of $C_1$, $C_2$, or $C_3$. Each of those subsets may be further subdivided into a number of aliquots. Beads in each aliquot may be coupled with a reactant of choice that has been fluorescently labeled with a fluorochrome associated with $C_4$ (e.g., Analyte A labeled with Cy3) under conditions such that the concentration or density of reactant bound to the beads of each aliquot will differ from that of each other aliquot in the subset. Alternatively, an entire subset may be treated with the $C_4$ fluorochrome under conditions that produce a heterogeneous distribution of $C_4$ reactant on beads within the subset. The subset may then be sorted with a cell sorter on the basis of the intensity of $C_4$ to yield further subsets that differ from one another in $C_4$ intensity.

One limitation of the alternative embodiment of using $C_4$ labeled reactant as a classification agent is that one must design the system so that the value of $C_4$ as a classification parameter is not lost. Therefore, one must take care to assure that the $C_4$ intensities of all subsets carrying reagent A differs from the $C_4$ intensities of all subsets carrying reagents B, C, and so forth. Otherwise, $C_4$ would not be useful as a parameter to discriminate reactant A from reactant B, etc.

With either embodiment, the number of subsets that can be prepared and used in practice of the invention is theoretically quite high, but in practice will depend, inter alia, on the level of homogeneity within a subset and the precision of the measurements that are obtained with a flow cytometer. The intra-subset heterogeneity for a given parameter, e.g., forward angle light scatter $C_1$, correlates inversely with the number of different subsets for that parameter that can be discriminated by flow cytometric assay. It is therefore desirable to prepare subsets so that the coefficients of variation for the value of each classification parameter ($C_1$, $C_2$, $C_3$, and $C_4$) to be used in a given analysis is minimized. Doing this will maximize the number of subsets that can be discriminated by the flow cytometer. Bead subsets may be subjected to flow cytometric sorting or other procedures at various different points in preparation or maintenance of the bead subsets to increase homogeneity within the subset. Of course, with simple assays designed to detect only a few different analytes, more heterogeneity can be allowed within a subset without compromising the reliability of the assay.

In an illustrative embodiment set forth here to explain one manner in which the invention can work in practice, the beads are used to test for a variety of antibodies in a fluid sample. A panel of bead subsets having known varying $C_1$, $C_2$, $C_3$, and $C_4$ values is first prepared or otherwise obtained. The beads within each subset are then coupled to a given antigen of interest. Each subset receives a different antigen. The subsets are then pooled to form an assay beadset and may be stored for later use and/or sold as a commercial test kit.

In the assay procedure, the beads are mixed with the fluid to be analyzed for antibodies reactive with the variety of antigens carried on the beads under conditions that will permit antigen-antibody interaction. The beads are labeled with a "secondary" reagent that binds to anti bodies bound to the antigens on the beads and that also bears the measurement fluorochrome associated with parameter $F_m$ (e.g., fluorescein). A fluoresceinated antibody specific for immunoglobulin may be used for this purpose. The beads are then run through a flow cytometer, and each bead is classified by its characteristic classification parameters as belonging to subset-1, subset-2, etc. At the same time, the presence of antibodies specific for antigen A, B, etc., can be detected by measuring green fluorescence, $F_m$, of each bead. The classification parameters $C_1$, $C_2$, $C_3$, and $C_4$ allow one to determine the subset to which a bead belongs, which serves as an identifier for the antigen carried on the bead. The $F_m$ value of the bead indicates the extent to which the antibody reactive with that antigen is present in the sample.

Although assays for antibodies were used above as an illustration, those of ordinary skill in the art will recognize that the invention is not so limited in scope, but is widely applicable to detecting any of a number of analytes in a sample of interest. For example, the methods described here may be used to detect enzymes or DNA or virtually any analyte detectable by virtue of a given physical or chemical reaction. A number of suitable assay procedures for detection and quantification of enzymes and DNA (particularly as the result of a PCR process) are described in more detail below.

5. BRIEF DESCRIPTION OF DRAWINGS

FIG. 5 shows a baseline data acquisition table for an illustrative multiple analyte assay in accordance with the invention.

FIG. 6 shows an assay definition table in accordance with the invention.

FIG. 7 shows a discriminant table for an illustrative multiple analyte assay in accordance with the invention.

FIG. 10 shows a results table for an illustrative multiple analyte assay in accordance with the invention.

FIG. 11 shows a interpretation table for an illustrative multiple analyte assay in accordance with the invention.

FIGS. 13a through 13e show an assay database in accordance with the invention for a specific experimental example.

6. DETAILED DESCRIPTION OF SPECIFIC EMBODIMENTS

Figure 1:
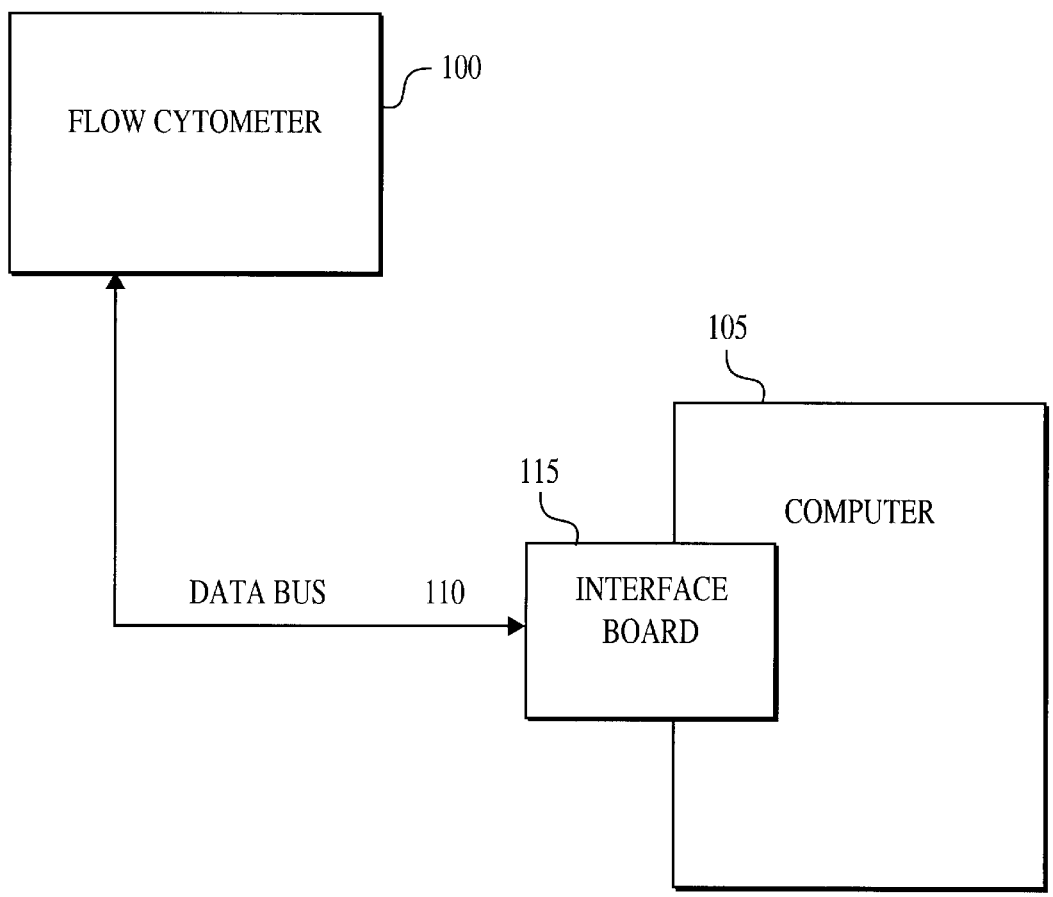
FIG. 1 is a block diagram of an illustrative hardware system for performing a multiplex assay method in accordance with the invention.

According to the present invention, assay components and methods for the measurement of enzymes, DNA fragments, antibodies, and other biomolecules are provided. The inventive technology improves the speed and sensitivity of flow cytometric analysis while reducing the cost of performing diagnostic and genetic assays. Further, and of tremendous significance, a multiplexed assay in accordance with the invention enables the simultaneous automated assay of multiple (at least an order of magnitude greater than available in the prior techniques) biomolecules or DNA sequences in real-time.

As those of ordinary skill in the art will recognize, the invention has an enormous number of applications in diagnostic assay techniques. Beadsets may be prepared, for example, so as to detect or screen for any of a number of sample characteristics, pathological conditions, or reactants in fluids. Beadsets may be designed, for example, to detect antigens or antibodies associated with any of a number of infectious agents including (without limitation, bacteria, viruses, fungi, mycoplasma, rickettsia, chlamydia, and protozoa), to assay for autoantibodies associated with autoimmune disease, to assay for agents of sexually transmitted disease, or to assay for analytes associated with pulmonary disorders, gastrointestinal disorders, cardiovascular disorders, and the like. Similarly, the beadset may be designed to detect any of a number of substances of abuse, environmental substances, or substances of veterinary importance. An advantage of the invention is that it allows one to assemble a panel of tests that may be run on an individual suspected of having a syndrome to simultaneously detect a causative agent for the syndrome.

Suitable panels may include, for example, a tumor marker panel including antigens such as prostate-specific antigen (PSA), carcinoembryonic antigen (CEA), and other suitable tumor markers; a regional allergy panel including pollen and allergens tested for by allergists of a particular region and comprising allergens known to occur in that region; a pregnancy panel comprising tests for human chorionic gonadotropin, hepatitis B surface antigen, rubella virus, alpha fetoprotein, 3', estradiol, and other substances of interest in a pregnant individual; a hormone panel comprising tests for T4, TSH, and other hormones of interests; an autoimmune disease panel comprising tests for rheumatoid factors and antinuclear antibodies and other markers associated with autoimmune disease; a blood borne virus panel and a therapeutic drug panel comprising tests for Cyclosporin, Digoxin, and other therapeutic drugs of interest.

6.1 Bead Technology

An important feature of the flow cytometric technology and techniques described here is the fabrication and use of particles (e.g., microspheres or beads that make up a beadset). It is through the use of appropriately labeled homogeneous bead subsets, combined to produce a pooled beadset, that the instant multiplexed assay method is practiced. Beads suitable for use as a starting material in accordance with the invention are generally known in the art and may be obtained from manufacturers such as Spherotech and Molecular Probes. Once a homogeneous subset of beads is obtained, the beads are labeled with an appropriate reactant such as a biomolecule, DNA sequence, and/or other reactant. Known methods to incorporate such labels include polymerization, dissolving, and attachment.

6.2 A Method for the Multiplexed Assay of Clinical Samples

Development of a multiplexed assay for use in accordance with the invention can be divided into three phases: (1) preprocessing, (2) real-time analysis, and (3) interpretation. During the preprocessing phase, baseline data is collected independently, via flow cytometric techniques, for each of an assay's bead subsets. Baseline data is used to generate a set of functions that can classify any individual bead as belonging to one of the assay's subsets or to a rejection class. During the analysis phase, flow cytometric measurements are used to classify, in real-time, each bead within an exposed beadset according to the aforementioned functions. Additionally, measurements relating to each subset's analyte are accumulated. During the interpretation phase the assay's real-time numerical results are associated with textual explanations and these textual explanations are displayed to a user.

The inventive method allows the detection of a plurality of analytes simultaneously during a single flow cytometric processing step. Benefits of the inventive multiplex assay method include increased speed and reduced cost to analyze a clinical sample.

6.2(a) System Hardware

FIG. 1 shows, in block diagram form, a system for implementing the inventive multiplexed assay method. Flow cytometer 100 output consists of a series of electrical signals indicative of one or more specified measured characteristics on each bead processed. These measurement signals are transmitted to computer 105 via data bus 110 and interface board 115. During the preprocessing phase, the signals are used by the computer to generate an assay database. During the real-time analysis phase, the signals are processed by the computer (using the assay database) in accordance with the inventive method to produce a multiplexed/simultaneous assay of a clinical sample.

Flow cytometer 100 operates in a conventional manner. That is, beads are processed by illuminating them, essentially one at a time, with a laser beam. Measurements of the scattered laser light are obtained for each illuminated bead by a plurality of optical detectors. In addition, if a bead contains at least one appropriate fluorescing compound it will fluoresce when illuminated. A plurality of optical detectors within the flow cytometer measure fluorescence at a plurality of wavelengths. Typical measured bead characteristics include, but are not limited to, forward light scatter, side light scatter, red fluorescence, green fluorescence, and orange fluorescence. One of ordinary skill in the use of flow cytometric techniques will recognize that the use of green fluorescent markers or labels can cause cross-channel interference between optical detectors designed to detect green and orange wavelengths (e.g., approximately 530 nanometers and approximately 585 nanometers respectively). A training set of beads, in combination with standard data manipulation, can correct for this cross-channel interference by providing the physical measurements required for mathematical correction of the fluorescence measurements.

One of ordinary skill will further recognize that many alternative flow cytometer setups are possible. For instance, additional color sensitive detectors could be used to measure the presence of other fluorescence wavelengths. Further, two or more laser beams can be used in combination to illuminate beads as they flow through the cytometer to allow excitation of fluorochromes at different wavelengths.

Computer 105 can be a conventional computer such as a personal computer or engineering workstation. In one embodiment, the computer is a personal computer having an Intel "486" processor, running Microsoft Corporation's "WINDOWS" operating system, and a number of ISO expansion slots.

Interface board 115 is designed to plug into one of the computer's 100 ISA (Industry Standard Architecture) expansion slots. While the design of an interface board is, in general, different for each specific type of flow cytometer 100, its primary functions include (1) receiving and parsing measurement data signals generated by the flow cytometer's detectors, (2) receiving control parameter status information from the flow cytometer, and (3) sending control parameter commands to the flow cytometer. The precise manner in which these functions are carried out are dependent upon the type (make and model) of the flow cytometer used. In one embodiment, employing a Becton-Dickinson "FACSCAN" flow cytometer, the interface board uses control signals generated by the flow cytometer to distinguish measurement data and flow cytometer parameter and control signals. Measured data include forward light scatter, side light scatter, red fluorescence, green fluorescence, and orange fluorescence. Parameter and control signals include flow cytometer amplifier gain adjustments and status information.

While the design of an interface board 115 for use with the inventive assay method would be a routine task for one skilled in the art of diagnostic medical equipment design having the benefit of this disclosure, an important aspect for any interface board is its ability to accommodate the transmission data rate generated by whatever flow cytometer is used. For example, the "FACSCAN" flow cytometer can transmit a 16-bit (2 byte) word every 4 microseconds resulting in burst data rates of 500,000 bytes per second. Microfiche appendix A provides a detailed source code embodiment of the inventive assay method for use with the "FACSCAN" flow cytometer.

Data bus 115 provides a physical communication link between the flow cytometer 100 and the interface board 110. Its physical and electrical characteristics (e.g., data width and bandwidth) are dependent upon the capabilities of the flow cytometer. It is noted that the data bus need not be a totally digital bus. If the flow cytometer does not include analog-to-digital conversion of measured bead characteristics (e.g., light scatter and fluorescence signals), then the data bus must communicate these analog signals to the interface board. It is then necessary that digital conversion of these signals be provided by either the interface board or another peripheral device before the data is transmitted to the computer 105.

6.2(b) System Software

Figure 2:
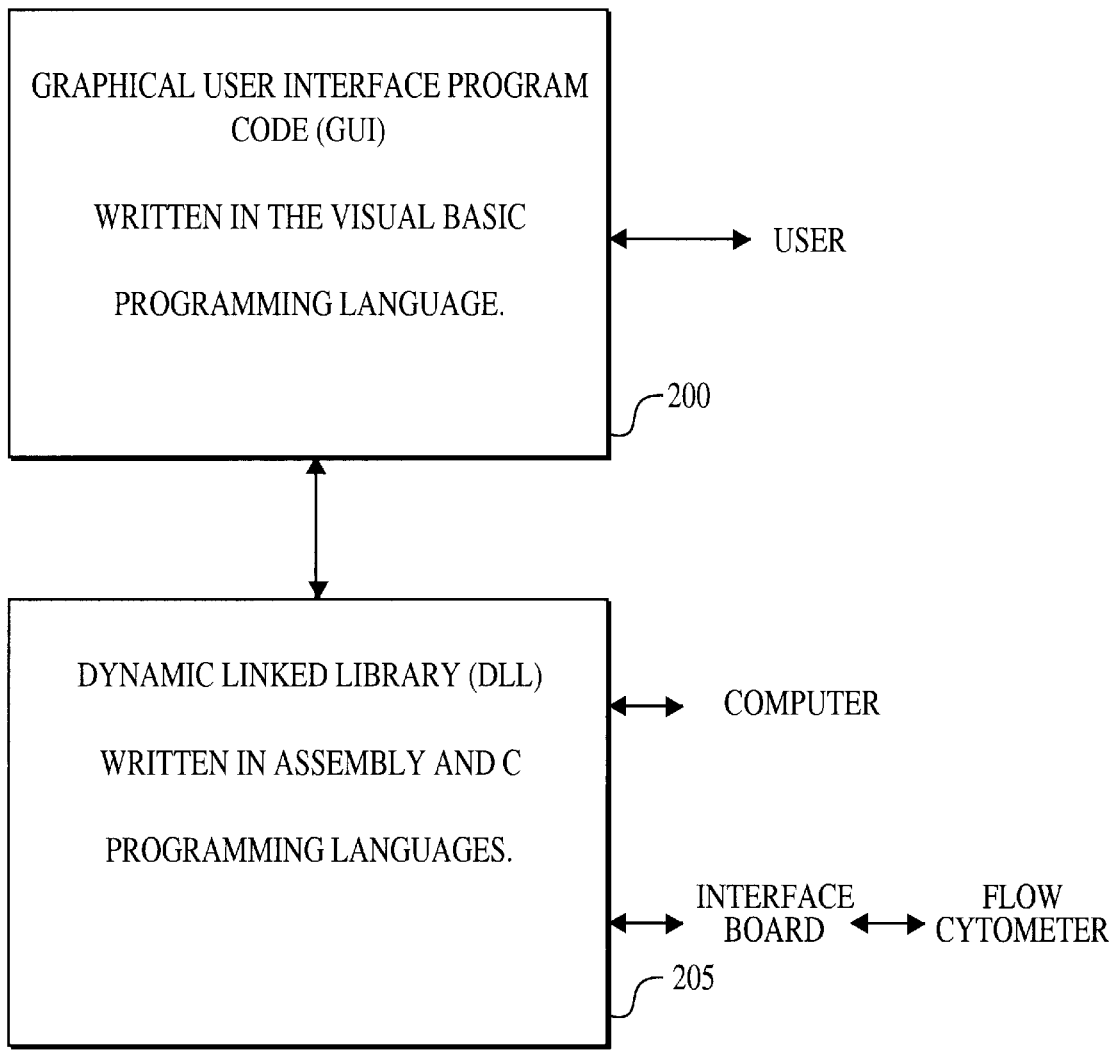
FIG. 2 is a block diagram of an illustrative software system for performing a multiplex assay method in accordance with the invention.

As shown in FIG. 2, the software architecture for the inventive assay method can be divided into two parts. A graphical user interface (GUI) 200 provides the means by which a user (1) receives assay results and (2) interacts with the flow cytometer. A dynamically linked library (DLL) 205 provides the means through which the inventive real-time assay is performed and includes routines necessary to (1) interact with interface board 115 and (2) send and receive information to the flow cytometer 100.

An important aspect of the inventive assay method is that it performs a simultaneous analysis for multiple analytes in real-time. One of ordinary skill in the art of computer software development will realize that real-time processing can impose severe time constraints on the operational program code, i.e., the DLL 205. For example, the "FACSCAN" flow cytometer can process, or measure, approximately 2,000 beads per second, where each bead is associated with eight 16-bit data values. Thus, to process flow cytometer data in real-time from a "FACSCAN," the DLL should be able to accept, and process, at a consistent data rate of at least 32,000 bytes per second. The need to accommodate this data rate, while also having sufficient time to perform real-time analysis based on the data, will generally necessitate that some of the DLL code be written in assembly language.

In a current embodiment, the GUI 200 is implemented in the visual basic programming language and the DLL 205 is implemented in C and assembly language programming. Microfiche appendix A contains source code listings for one embodiment of the GUI and DLL.

6.2(c) Preprocessing

Figure 3:
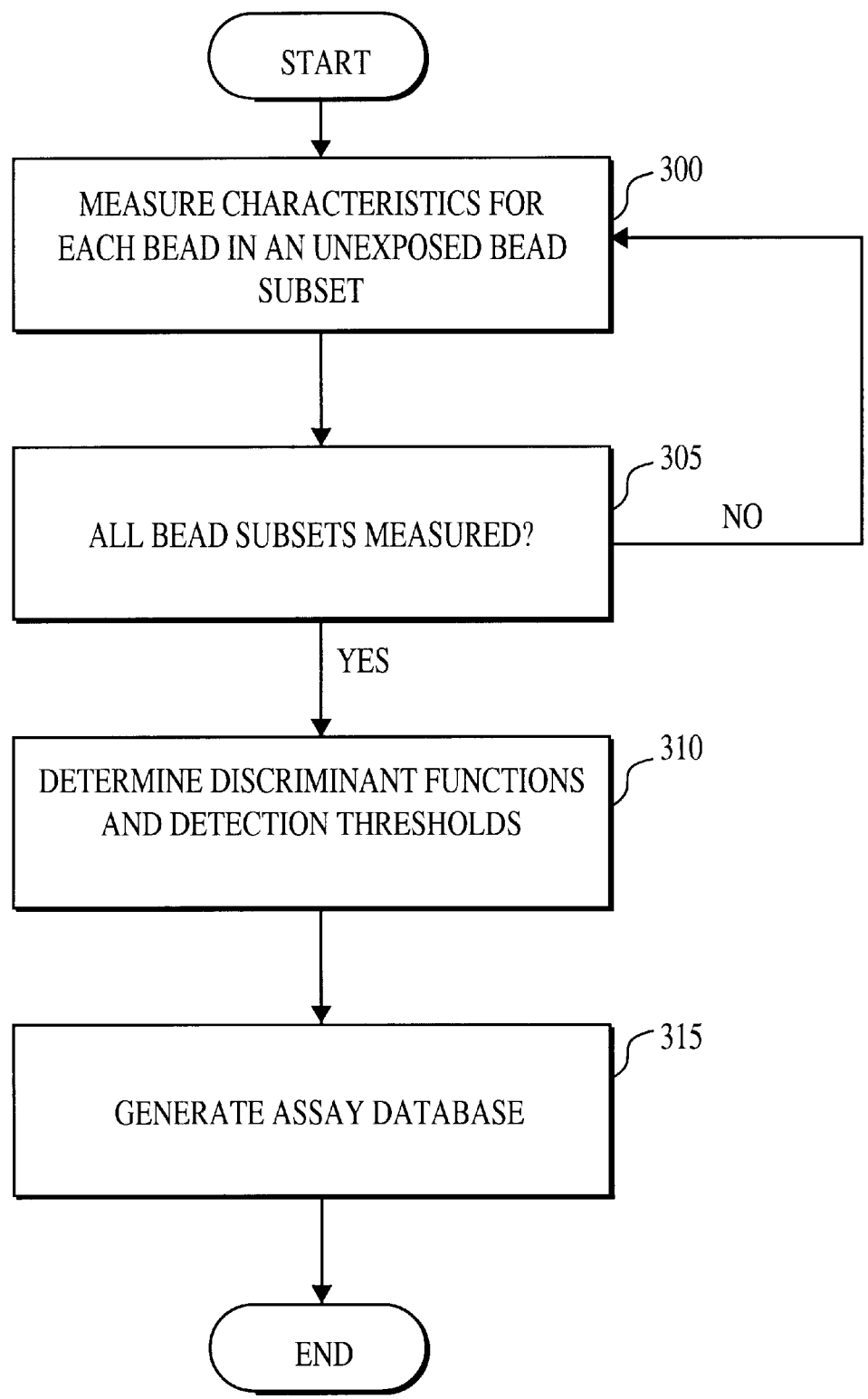
FIG. 3 is a flow-chart for a preprocessing phase in accordance with the inventive multiplexed assay method.

A function of the preprocessing phase is to generate an assay database for use during the real-time analysis of an exposed beadset (clinical sample). Thus, preprocessing is performed prior to combining separately labeled bead subsets to form assay beadsets. Assay definition, discriminant function definition, and interpretation tables are created at the time an assay beadset is created. FIG. 3 shows, in flow chart form, the steps taken during the preprocessing phase.

A bead subset is characterized by (1) the analyte it is designed to identify, (2) one or more classification parameters $C_1 \ldots C_n$, and (3) one or more measurement parameters $F_{m1}-F_{mx}$. During the preprocessing phase the classification parameters are used to generate a set of functions, referred to as discriminant functions, that can classify a bead as belonging to one of the assay's subsets or a rejection class. Measurement parameters are used during the real-time analysis phase to determine if a specified analyte is present in the clinical sample being analyzed.

The precise number of individual beads contained in any given subset is relatively unimportant, the only significant criterion being that a sufficient number are used so that a good statistical characterization of the subset's parameters can be achieved during the real-time analysis phase. In a current embodiment, each bead subset contains an equal number of beads. One of ordinary skill in the field will recognize that the precise number of beads within any given bead subset can vary depending upon many factors including, but not limited to, the number of analytes an assay beadset is designed to detect, the uniformity of the labeled beads (with respect to each of the measured parameters $C_1 \ldots C_n, F_{m1} \ldots F_{mx}$), and the penalty of misclassifying (e.g., making a type 1 or type 2 classification error) a bead during analysis.

During preprocessing, each bead in an unexposed subset is measured by a flow cytometer 100 and the resulting data values accumulated for later use 300. For example, if the flow cytometer measures n classification parameters and x measurement parameters, i.e., generates (n +x) values for each bead, data for each of the subset's (n+x) parameters are updated based on each bead's measurements. This data collection step is repeated independently for each subset in the assay's beadset 305. The collection of such data for each of an assay's subsets constitutes an assay's baseline data.

After an assay's baseline data has been collected, a set of discriminant functions are determined 310. During real-time analysis, the discriminant functions are used to classify a bead into one of the assay's bead subsets or a rejection class based solely on the measured classification parameters, $C_1 \ldots C_n$. This step, in principle and practice, is a problem of multi-dimensional classification or cluster analysis. Many prior art techniques and commercial software programs exist to perform this task.

Beads are generally manufactured in large quantities referred to as batches. Each bead in a batch is of nearly identical size and has substantially the same dye absorption capacity. In light of this manufacturing process, bead subsets can be created using precise dilutions of chosen dyes and, because of their nearly identical size, all classification parameters will exhibit essentially equal variances. By correcting for scaling of the photo-multipliers within a flow cytometer, a linear classification rule can be generated. Further, since there are equal quantities of beads in each subset, the prior probabilities will be equal. This allows use of Fisher's linear discriminant technique to calculate the discriminant functions which define classification boundaries. See, Fisher, "The Use of Multiple Measurements in Taxonomic Problems," Annals of Eugenics, 7, 179–188 (1936). For instance, linear hierarchical discriminant functions may be chosen which are equidistant, in a Euclidean sense, between the centers or centroids of any two of an assay's bead subsets. Notwithstanding the present example, other types of discriminant functions, such as quadratic functions and those discriminating on more than two classification parameters at once, are also possible.

In addition to the discriminant functions, a set of threshold values are chosen which are used during the real-time analysis phase to detect the presence of a target analyte. For example, assume measurement parameter $F_{m1}$ is used to detect analyte-A. During preprocessing, the baseline or unexposed value for $F_{m1}$ is measured and accumulated for that subset's beads. Analyte-A's threshold could then, for example, be set to $F_{m1}$'s baseline mean value plus one standard deviation of $F_{m1}$'s baseline value. One of ordinary skill will recognize that the precise function or value selected for a threshold depends upon the parameter being measured (e.g., its distribution) and the cost of making a classification error (e.g., a type 1 or a type 2 error). It is routine that such values be based on an empirical review of the baseline data. The important criterion is that the threshold reliably distinguish between the presence and absence of the target analyte in an exposed assay beadset.

After baseline data for each of an assay's bead subsets are collected and discriminant functions and analyte threshold values are established, an assay database is generated 315.

Assay Database

Figure 4:
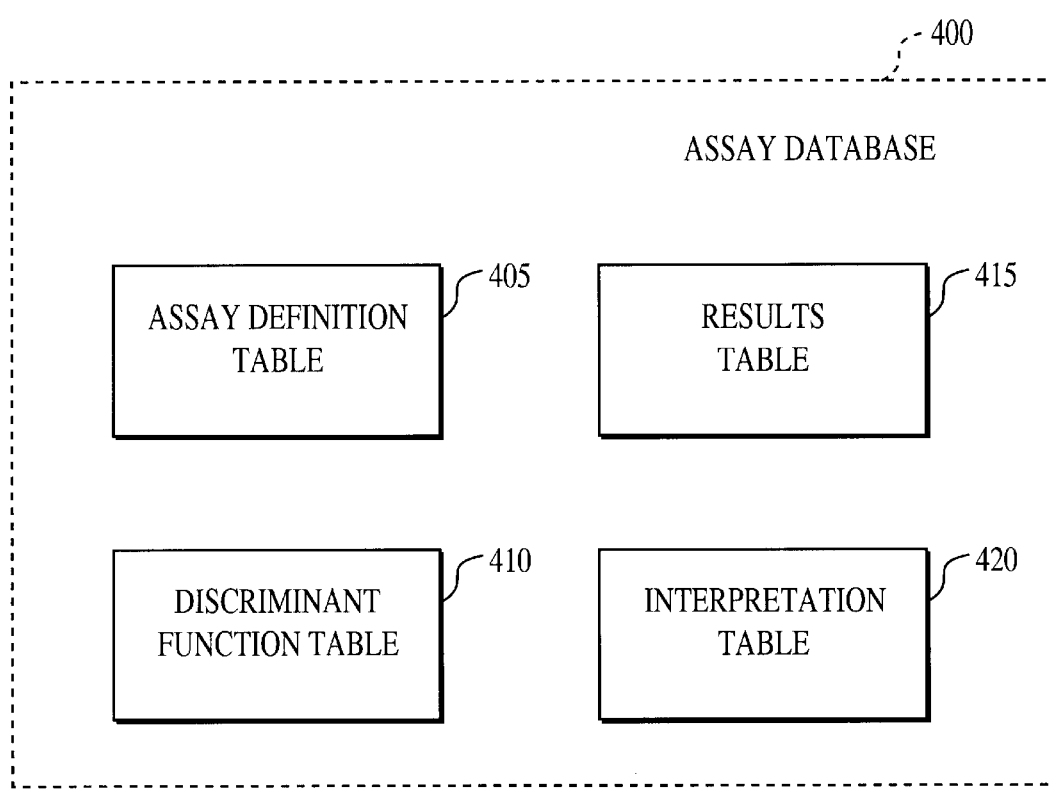
FIG. 4 shows an assay database in accordance with the invention.

As shown in FIG. 4, an assay database 400 consists of an assay definition table 405, a discriminant function table 410, a results table 415, and an interpretation table 420. See FIG. 4.

The assay definition table 405 defines an assay which, as described above, comprises two or more bead subsets each of which is designed to detect a specified analyte. Each row in the assay definition table describes a bead subset and contains the following entries: (1) assay name, (2) subset name, (3) subset token, (4) baseline values for each of the subset's measurement parameters $F_{m1}$–$F_{mx}$, and (5) test-type token. The subset name entry is a text string identifying the subset by, for example, the type of analyte it is labeled to detect. The subset token is a unique subset identifier. The measurement parameter baseline entries are used during the interpretation phase to associate a numerical result (collected during the real-time analysis of a clinical sample) with a textual output string. Finally, the test-type token identifies which one of a possible plurality of interpretation tests to perform on the collected (real-time) data during the interpretation phase.

The discriminant function table 410 is used to systematically set forth an assay's set of discriminant functions. Each row in the discriminant function table implements a single discriminant function and includes entries for (1) the assay's name, (2) a unique row identifier, (3) one or more classification parameters upon which to evaluate, (4) high and low discriminant values for each of the listed classification parameters, and (5) evaluation tokens which are assigned as a result of evaluating the discriminant function.

The results table 415 is used to store, or accumulate, data on an assay's beadset during the real-time analysis phase of the inventive method and is discussed further in Section 6.2(d).

The interpretation table 420 provides a means to associate text messages with each enumerated assay result and is discussed further in Section 6.2(e).

Preprocessing Example

Consider an assay beadset designed to simultaneously detect four analytes: analyte-A, analyte-B, analyte-C, and analyte-D. Thus, the assay's beadset is comprised of four bead subsets, each labeled for a different analyte. Suppose further that the assay beadset is to be processed by a Becton-Dickinson Immunocytometry Systems "FACS-CAN" flow cytometer. For each bead processed, the "FACSCAN" measures forward light scatter, side light scatter, red fluorescence, orange fluorescence, and green fluorescence. Let classification parameter $C_1$ be forward light scatter, classification parameter $C_2$ be side light scatter, classification parameter $C_3$ be red fluorescence, classification parameter $C_4$ be orange fluorescence, and measurement parameter $F_{m1}$ be green fluorescence. (This notation implies that each bead in a subset is labeled with a green fluorophore bearing, for example, an antibody or dye specifically targeted to that subset's analyte.)

After preparing each of the four subsets and before they are combined to form the assay beadset, they are processed by the flow cytometer and their measured data are accumulated: values for each of the parameters $C_1$, $C_2$, $C_3$, $C_4$, and $F_m$ are recorded for each bead. Each bead subset is similarly processed. Completion of this task constitutes completion of baseline data acquisition.

Using baseline data, the assay's beads are clustered in the four-dimensional parameter space defined by $C_1$, $C_2$, $C_3$, and $C_4$. The result of this cluster analysis is that each subset is characterized by a mean ($\mu$) and standard deviation ($\sigma$) for each of its four classification parameters. See FIG. 5. As previously noted, the precise number of individual beads contained in any given bead subset can be calculated by those of ordinary skill in the art. This calculation is required to obtain good statistical characterization of the subset's parameters—e.g., small, or relatively fixed, coefficient of variations for each parameter.

As shown in FIG. 6, the assay definition table 405 is comprised of general information relevant to the overall diagnostic function of the assay. For instance, in a genotyping assay, each of the assay's subset's may be assigned a token used for identification: e.g., token 46 represents the bead subset labeled to detect a wildtype coding sequence for a specified gene; subset tokens 21, 50, and 5 represent subsets labeled to detect various mutant type coding sequences for a specified gene(s). Additionally, measurement parameter $F_{m1}$'s baseline (in this example the mean) and standard deviation values are listed. Finally, a test-type token is listed. In the current embodiment a test-type token of '0' means an OVER/UNDER interpretation test is to be performed and a test-type token of '1' means a SHIFT interpretation test is to be performed. See Section 6.2(f) for further discussion of these issues.

Discriminate functions are generated by viewing the assay's baseline data graphically in three dimensions and creating planes to separate the different subset clusters. These "planes" are created by applying Fischer's Linear Discriminant to the n-dimensional classification parameter space. A populated discriminate function table based on the baseline data of FIG. 5 is shown in FIG. 7.

The discriminant function table provides a systematic means of evaluating a series of classification values ($C_1$, $C_2$, $C_3$, $C_4$) in order to classify a bead. In general bead classification proceeds by entering the discriminant function table at row 0, performing a test on a specified parameter (e.g., $C_1$, C2, $C_3$, or $C_4$) and then, depending upon the result, either classifying the bead or proceeding to another test which involves evaluating a different row in the table. For example, suppose bead A has the following measured classification parameter values: $C_1=V_1$, $C_2=V_2$, $C_3=V_3$, and $C_4=V_4$. Classification of bead A via the discriminant function table of FIG. 7 begins as follows (the pseudo-code below would demonstrate to those skilled in the art of programming the logic involved in the classification process):

1. Enter table at row 0 with measured values for $C_1$, $C_2$, $C_3$, and $C_4$.
2. If (LOW VALUE=500)$\leq$(PARAMETER=$C_1$=$V_1$)$\leq$ (HIGH VALUE=620) then (result=TRUE), else (result= FALSE).
3. If (result=TRUE) and (TRUE ROW ID$\neq$0), then re-enter table at TRUE ROW ID, else
4. If (result=TRUE) and (TRUE ROW ID=0), then (class= TRUE TOKEN).
5. If (result=FALSE) and (FALSE ROW ID$\neq$0), then re-enter table at (row=FALSE ROW ID), else
6. If (result=FALSE) and (FALSE ROW ID=0), then (class= FALSE TOKEN).
7. If (TRUE TOKEN or FALSE TOKEN)=0, then (class= reject class).

Figure 8:
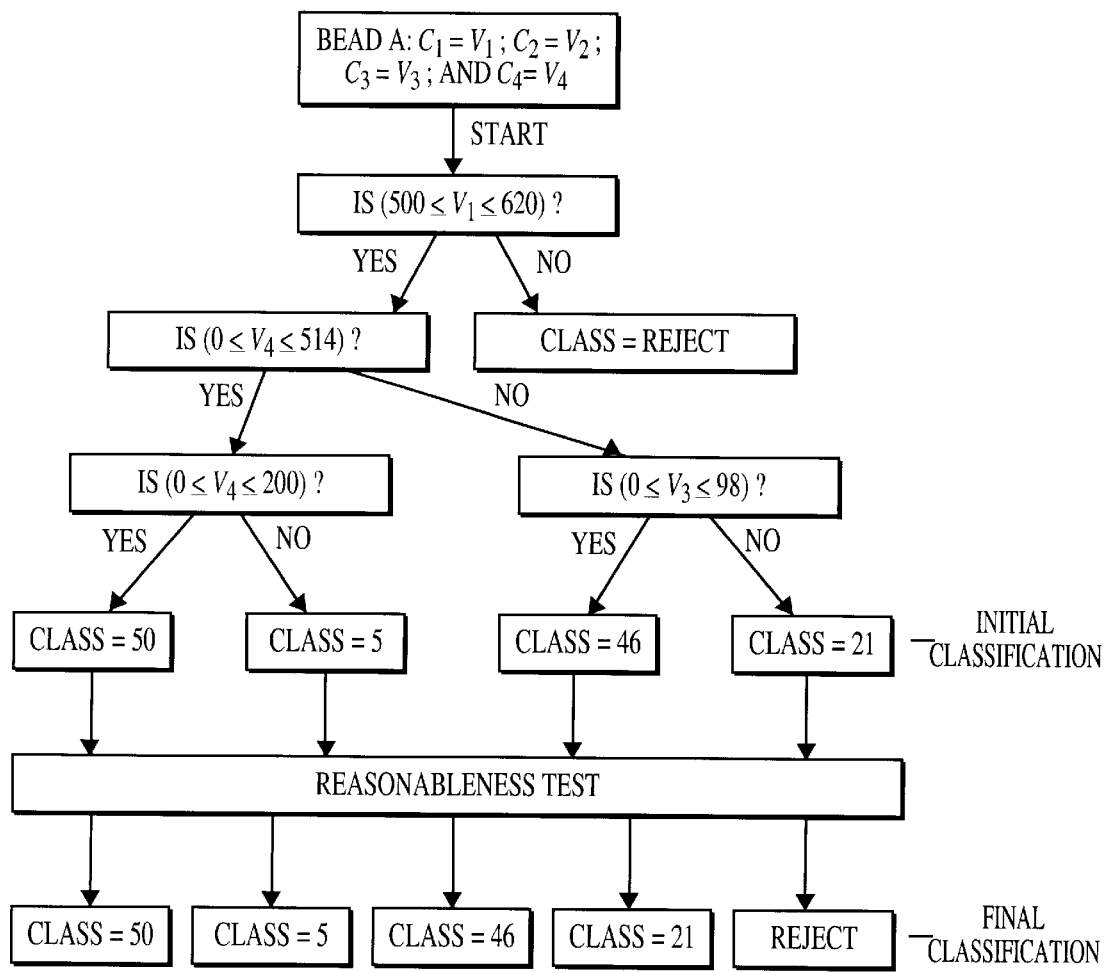
FIG. 8 shows a decision tree view of the illustrative discriminant function table of FIG. 7.

One of ordinary skill will recognize from the above discussion that a discriminant function table embodies a (classification) decision tree. FIG. 8 shows this relationship for the discriminant function table of FIG. 7 explicitly. A discussion of the discriminant function table as it relates to the real-time processing of an exposed assay beadset is provided in Section 6.2(d). Once a beadset is preprocessed, the data may be employed in real-time analysis of many assays using that set.

6.2(d) Real-Time Analysis

Once a collection of bead subsets have been characterized as described above and combined to form an assay beadset, the beadset may be exposed to a test sample. That is, they may be used to analyze a clinical sample. After exposure the beadset is ready for real-time analysis. The real-time analysis phase is initiated by installing the exposed beads into a conventional flow cytometer for processing.

As described above, for each bead processed a flow cytometer 100 generates electrical signals indicative of a plurality of measured parameters, $C_1 \ldots C_n$, $F_{m1} \ldots F_{mx}$. These values are transmitted to computer 105 via data bus 110 and interface board 115. Values for a bead's classification parameters $C_1 \ldots C_n$ are used to evaluate the assay's discriminant functions, as encoded in a discriminant function table 410, the result of which is an initial classification of the bead into one of the assay's bead subsets or a reject class.

After this initial classification, a bead's measured classification parameter values $C_1 \ldots C_n$ can be checked against their ($C_1 \ldots C_n$) baseline values to determine if it is "reasonable" to classify the bead as belonging to the initially identified class. In a current embodiment, this reasonableness test is implemented by computing the distance between the measured classification parameter values and the mean values obtained during preprocessing. If the measured values for $C_1 \ldots C_n$ for a particular bead are sufficiently distant from the identified subsets baseline values, the bead is assigned to a reject class. Use of this technique allows for the rejection of beads that were initially misclassified and improves the overall reliability of the analysis.

To ensure proper classification, a preferred embodiment's pooled beadset will include a bead subset which has no bound reactants (e.g., a placebo bead subset) in a known ratio to the beadset's other subsets.

It is noted that when a beadset is comprised of beads manufactured in a single batch, the above described reasonableness test can be incorporated into the linear discriminant functions by creating reject space between all subsets. However, when a beadset is comprised of beads from more than one batch a Euclidean (or similar) distance measure is needed to validate the classification result.

Figure 9:
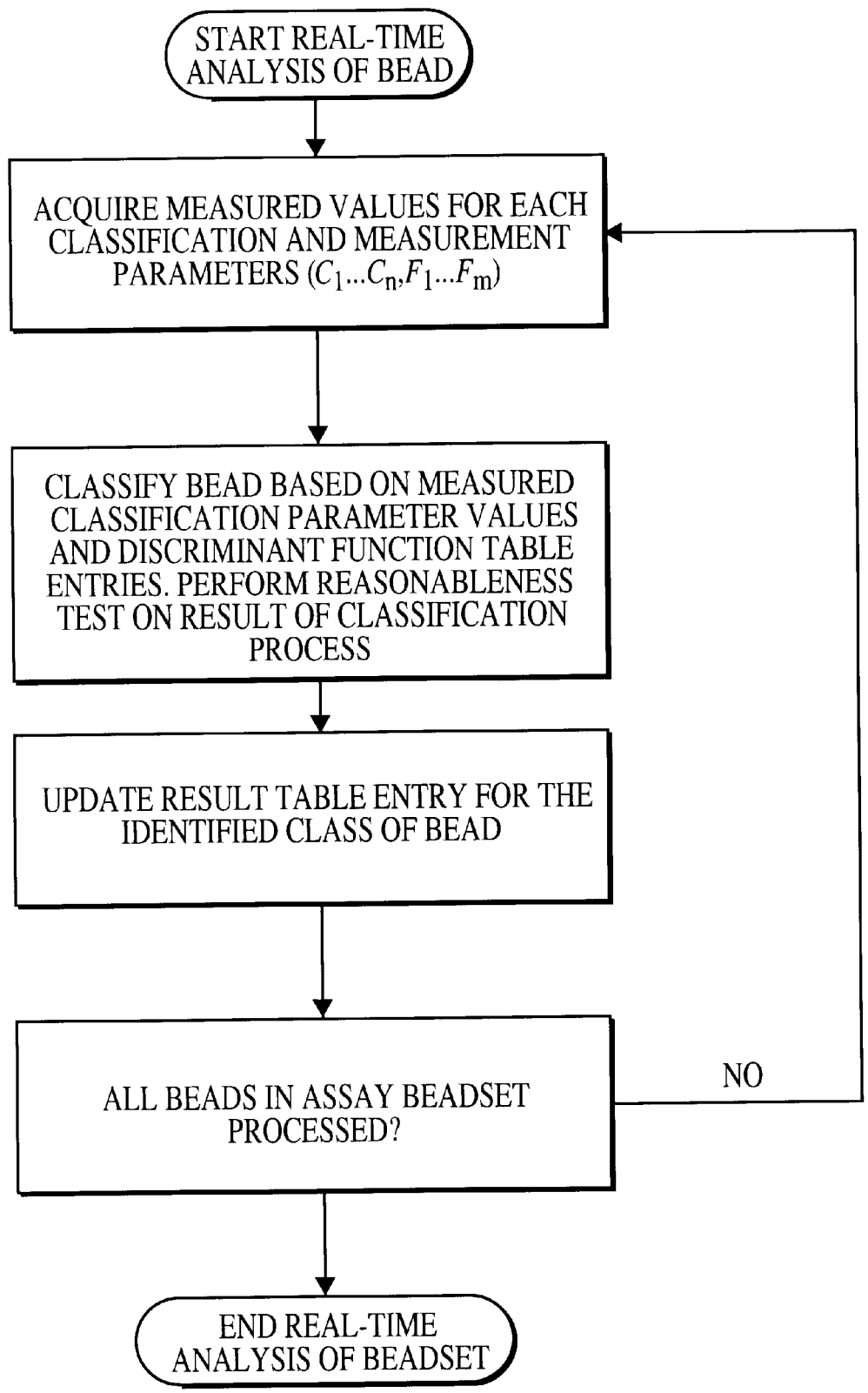
FIG. 9 is a flow-chart for a real-time analysis phase of a multiple analyte assay in accordance with the invention.

Once a bead is assigned its final classification, the assay's results table 415 is updated to reflect the newly classified bead's measurement parameter values $F_{m1} \ldots F_{mx}$. This data acquisition, classification, and update process is repeated for each bead in the assay beadset in real-time. FIG. 9 shows, in block diagram form, the general steps performed during the real-time analysis phase of a method in accordance with the invention.

In one embodiment the following data are accumulated in the results table for each class (subset) of bead in the assay: (1) total count of the number of beads detected in the specified class, (2) a running sum for each measurement parameter $F_{m1}$–$F_{mx}$, (3) for each measurement parameter the total count of the number of beads in the class whose measurement value is less than the parameter's baseline value, and (4) for each measurement parameter the total count of the number of beads in the class whose measurement value is more than the parameter's baseline value.

Real-Time Analysis Example

In the illustrative embodiment introduced in Section 6.2(c), the assay beadset is designed to simultaneously detect four analytes using four classification parameters ($C_1$ represents forward light scatter, $C_2$ represents side light scatter, $C_3$ represents red fluorescence, and $C_4$ represents orange fluorescence) and one measurement parameter ($F_{m1}$ representing green fluorescence). After exposing the beadset to a suitable biological sample, it is placed into a flow cytometer 100 which processes each bead (e.g., measures parameters $C_1$, $C_2$, $C_3$, $C_4$, and $F_{m1}$) and transmits to computer 105 signals indicative of these measurements via data bus 110 and interface board 115.

For each bead processed by the flow cytometer, values for $C_1$, $C_2$, $C_3$, and $C_4$ are evaluated in accordance with the discriminant function table shown in FIG. 7 to initially classify the bead as belonging to a particular subset, for example, in a genetic analysis intended to detect mutations in the Kras oncogene, the classification could proceed as follows: (1) class 46, Kras CODON 46 WILDTYPE, (2) class 21, Kras CODON 21 MUTANT, (3) class 50, Kras CODON 50 MUTANT, (4) class 5, Kras CODON 5 MUTANT, or (5) a reject class. (See FIG. 8 for a decision tree representation of the discriminate function table of FIG. 7.) If the bead is initially classified as belonging to any class except the reject class, a reasonableness test is performed on the bead's classification parameter values, $C_1$–$C_n$. For example, if the bead received an initial classification of class 50 and its $C_1$ value is more than two standard deviations away from its mean, the bead is given a final classification of reject. Otherwise the bead's final classification is the same as its initial classification-50.

If the bead's final classification is other than reject, its $F_{m1}$ value is used to update the assay's results table in the following manner (see FIG. 10):

1. Identifying, based on the bead's classification token (i.e., subset token 46, 21, 50, or 5), the row in the results table which is to be updated.
2. Incrementing the identified row's COUNT value. The COUNT value reflects the total number of beads of the specified class that have been identified during the analysis.
3. Adding the bead's $F_{m1}$ value to the value contained in the row's SUM column. The SUM value reflects a running sum of the identified classes measurement values.
4. If the bead's $F_{m1}$ value is greater than $F_{m1}$'s base value (determined during the preprocessing phase, see FIG. 6), then incrementing the row's OVER COUNT value. The OVER COUNT value reflects the total number of beads of the specified class that have been processed whose $F_{m1}$ values are above that of baseline.
5. If the bead's $F_{m1}$ value is less than $F_{m1}$'s base value (as determined during the preprocessing phase, see FIG. 6), then incrementing the rows UNDER COUNT value. The UNDER COUNT value reflects the total number of beads of the specified class that have been processed whose $F_{m1}$ values are below that of baseline.

In a preferred embodiment, data (i.e., count, and measured $F_{m1}$ values) for each bead classified as a reject can also be collected.

6.2(e) Interpretation

Following the real-time classification and accumulation of results as described above, the user may select to see a text based presentation or interpretation of the assay's numerical results. During the interpretation phase the assay's real-time numerical results are associated with textual explanations. These textual explanations can be displayed to the user.

It is the function of the interpretation table 420 to associate textual descriptions of an assay's possible outcomes with an actual assay's numerical results. Each row in the interpretation table provides the necessary information to make a single interpretation and typically includes entries for (1) the assay's name, (2) a subset token identifying the class or subset on which the interpretation is based, (3) an outcome identifier for the identified subset, (4) a test-type token, (5) high and low discriminant values for each measurement parameter utilized in the identified test, and (6) a text string describing the row's result.

The test-type token identifies which one of a possible plurality of interpretation tests to perform on the collected (real-time) data during the interpretation phase. In a current embodiment the test-type token is either '0' or '1'. A value of '0' indicates an OVER/UNDER interpretation test is to be performed. A value of '1' indicates a SHIFT interpretation test is to be performed. These tests are defined in the following manner:

$$OVER/UNDER\ Test\ Value = \frac{OVER\ COUNT}{UNDER\ COUNT},\ and$$

$$SHIFT\ Test\ Value = \frac{SUM/COUNT}{Baseline\ F_m\ Value},$$

where the variables OVER COUNT, UNDER COUNT, SUM, COUNT, and baseline $F_m$ are described above in Section 6.2(d).

The OVER/UNDER test is generally used for qualitative measurements where the level of reactivity of beads is an indication of the condition or concentration of a biomolecule present in the sample. The shift test is used where the result sought is a determination of the a minimally detectable level of a particular biomolecule. One of ordinary skill will recognize that many other tests could be performed. Examples include ranking, stratification, ratio of means to a standard, or to each other, etc.

In general an interpretation table 420 may associate any number of entries or interpretations (e.g., rows within the table) with a single assay class or bead subset. For instance, bead subset Y could have a single measurement parameter ($F_{m1}$) associated with it and this measurement parameter could indicate, depending upon its value, that one or more interpretations are appropriate.

Note, the contents of the interpretation table 420 are generated during the preprocessing phase. This implies that the target assay be understood and that the various assay results be considered prior to construction of multiplexed assays.

6.2(f) Interpretation Example

Consider again the assay beadset, introduced above, designed to simultaneously detect four analytes. FIG. 11 shows a sample interpretation table for this assay. Interpretation of the assay's real-time numerical results is initiated by, for example, the user selecting "interpret results" via the inventive method's graphical user interface.

Figure 12:
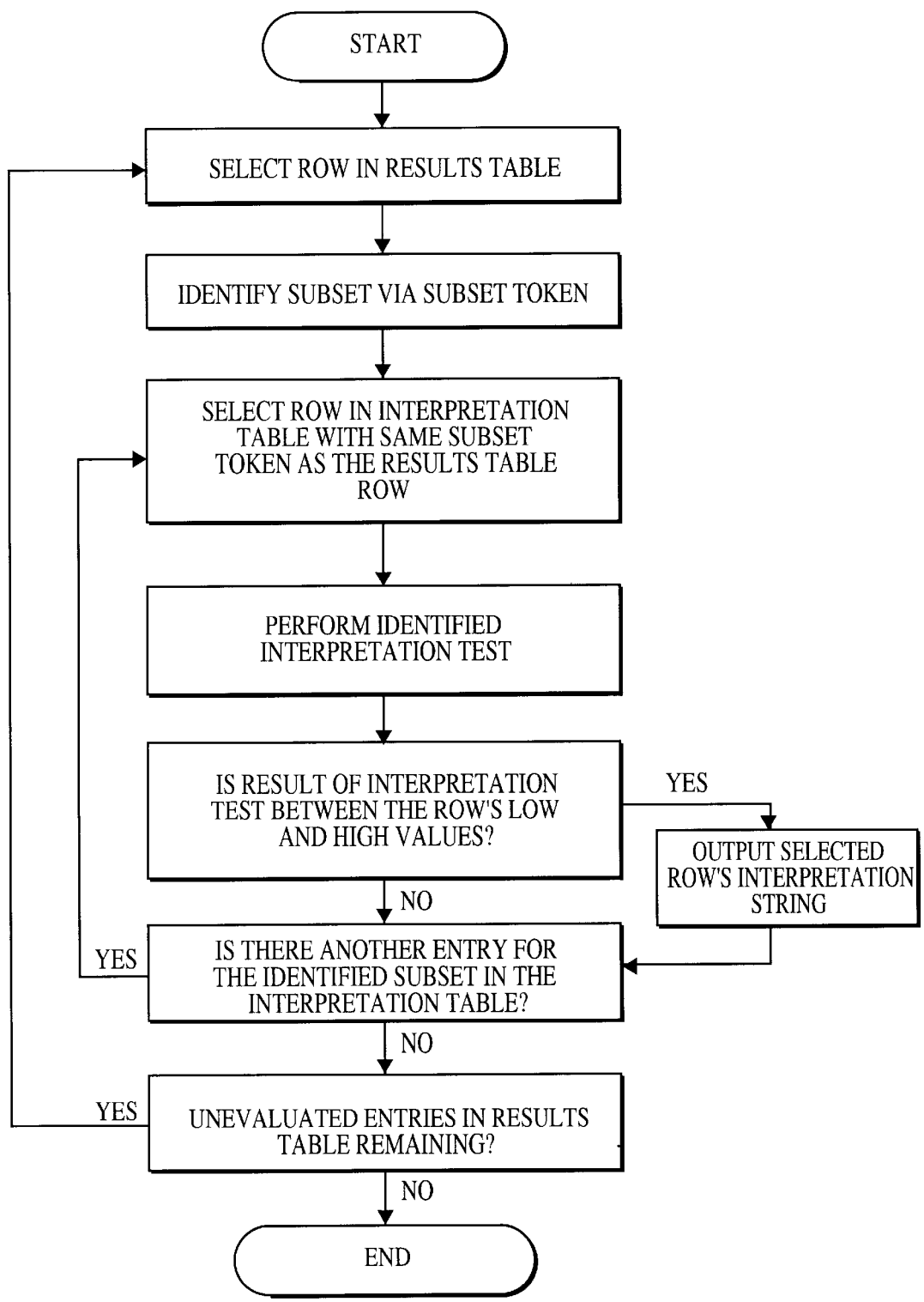
FIG. 12 is a flow-chart for an interpretation phase of a multiple analyte assay in accordance with the invention

As described above, each bead subset (class) within an assay has an entry or row in the results table, FIG. 10. The general procedure for interpreting an assay's real-time numerical results is shown in flow-chart form in FIG. 12. In general, each row of the results table is matched against every row in the interpretation table with the same subset token. If the result of performing the specified test is between the identified row's low and high values, then the associated textual message is displayed to the user. When all rows in the interpretation table for a single results table row have been checked, the next results table row is evaluated. This process is repeated until the every row in the interpretation table has been compared to the appropriate results table entry.

As a specific example, consider the interpretation of subset 50's (KRAS CODON 50 MUTANT, see FIG. 6) results table entry. The subset's token, 50, is used to identify three rows in the interpretation table (having outcome IDs of 1, 2, and 3) that contain information regarding evaluation of the mutant analyte. For the first identified row, the test-type token indicates a SHIFT type interpretation test is to be performed. Performing this test, as defined above, yields:

$$SHIFT\ Test\ Value = \frac{SUM/COUNT}{Baseline\ F_m\ Value} = \frac{1,700,000/1,000}{170} = 10$$

Next, the computed SHIFT test value is compared against each interval in the identified rows of the interpretation table. For the row having OUTCOME ID equal to 1, since (LOW VALUE=10)≦SHIFT Test Value=10≦(HIGH VALUE=667) is true, that row's INTERPRETATION entry—"identical complementary strand"—is displayed to the user. This process is repeated for subset 50's remaining two rows in the interpretation table. Further, this process is repeated for each row in the results table.

The result of the interpretation phase is a series of textual messages that describe the results of the assay. Conclusion of the interpretation phase marks the end of the assay.

6.2(g) Operational Considerations

Assay definition, discriminant function definition, and interpretation tables are created at the time an assay beadset is created. Baseline classification data is collected only once for a given assay. That is, once an assay is defined and its baseline data is obtained, any number of beadsets can be manufactured to perform the analysis. To allow this "sharing" of baseline data the assay beadset may contain a center or calibration bead subset.

As would be known to those of ordinary skill in the field, a calibration beadset can be used to adjust any given flow cytometer to a standard. Calibration beadsets are typically processed separately from an assay. Further, calibration is generally performed daily. The purpose of calibration is to adjust the sensitivity of a flow cytometeres photomultipliers to accommodate day to day and machine to machine differences.

Unlike prior art calibration techniques which are performed manually, the processing of a calibration beadset and the adjustment of flow cytometer operational parameters (e.g., photomultiplier voltages) is performed under software control automatically. See microfiche appendix A for embodiment details.

6.3 Antibody Detection

Assays for antibody are widely used in medicine and clinical analysis for an wide variety of purposes, from detection of infections to determination of autoantibody. The following example illustrates use of the inventive method in an antibody assay and assumes the use of a flow cytometer capable of providing at least five measurements for each bead processed: forward light scatter as classification parameter $C_1$, side light scatter as classification parameter $C_2$, red fluorescence as classification parameter $C_3$, orange fluorescence as classification parameter $C_4$, and green fluorescence as measurement parameter $F_{m1}$.

In one method a number of bead subsets, e.g., subsets 1 through 10 (identified as sS1–sS10), are prepared, for example, by using a cell sorter to sort a heterogeneous population to collect a homogeneous subset or alternatively, by preparing the beads using tightly controlled specifications to ensure production of a homogeneous subset. Each subset is distinguishable by its characteristic pattern of classification parameters $C_1$, $C_2$, $C_3$, and $C_4$. The beads in each subset are then labeled with a different antigen such as AgA, AgB, etc. so as to create a collection of labeled subsets as follows: sSI-AgA, sS2-AgB, sS3-AgC, sS4-AgD, sS5-AgE, sS6-AgF, sS7-AgG, sS8-AgH, sS9-AgI, and sS10-AgJ.

Antigens AgA through AgJ may be attached to the beads by any of a number of conventional procedures such as by chemical or physical absorption as described by Colvin et al., "The Covalent Binding of Enzymes and Immunoglobulins to Hydrophilic Microspheres" in Microspheres: Medical and Biological Applications, 1–13, CRC, Boca Raton, Fla., 1988; Cantarero et al., "The Adsorptive Characteristics of Proteins for Polystyrene and Their Significance in Solid-Phase Immunoassays," Anal Biochem, 105, 375–382 (1980); and Illum et al., "Attachment of Monoclonal Antibodies to Microspheres," Methods in Enzymol, 112, 67–84 (1985) 112, 67–84 (1985).

After attachment of antigen to the beads'surface, aliquots from each subset are mixed to create a pooled or assay beadset, containing known amounts of beads within each subset. Preferably, the pooled set is prepared with equal volumes of beads from each subset, so that the set contains about the same number of beads from each subset.

The assay beadset may then be incubated with a fluid sample of interest, such as serum or plasma, to test for the presence of antibodies in the fluid that are reactive with antigens on the beads. Such incubation will generally be performed under conditions of temperature, pH, ionic concentrations, and the like that facilitate specific reaction of antibodies in the fluid sample with antigen on the bead surface. After a period for binding of antibody, the beads in the mixture are centrifuged, washed and incubated (again under controlled conditions) for another period of time with a "secondary" antibody such as, for example, fluorescein labeled goat anti human immunoglobulin. The secondary antibody will bind to and fluorescently label antibodies bound to antigen on the beads. Again after washing (or without washing), the beads are processed by the flow cytometer and the four classification parameters forward light scatter, side light scatter, red fluorescence, and orange fluorescence are measured and used to identify the subset to which each bead in the assay beadset belongs. A simultaneous measurement of green fluorescence (measurement parameter) for each bead allows one to determine whether the bead has antibody bound to it. Because the subset to which a bead belongs is correlated with the presence of a particular antigen, e.g., sSI-AgA, one may readily determine the specificity of the antibody bound to a bead as a function of the subset to which it belongs.

Experimental Example

Three different antigen-antibody pairs were used in a multiplex experiment demonstrating the ability to detect the presence or absence of several antibodies in a single sample. Antibodies were coupled to latex microspheres via carbodiimide coupling, and the corresponding antibodies were fluorescently labeled with fluorescein isothiocyanate (green fluorescence-$F_m$). Each antigen was coupled to a unique microsphere. Baseline data for the fluorescent antibodies and antigen-microsphere complexes used in this experiment are shown in FIG. 13a. Baseline data for the three bead subsets of FIG. 13a are given in FIG. 13b.

Figure 14:
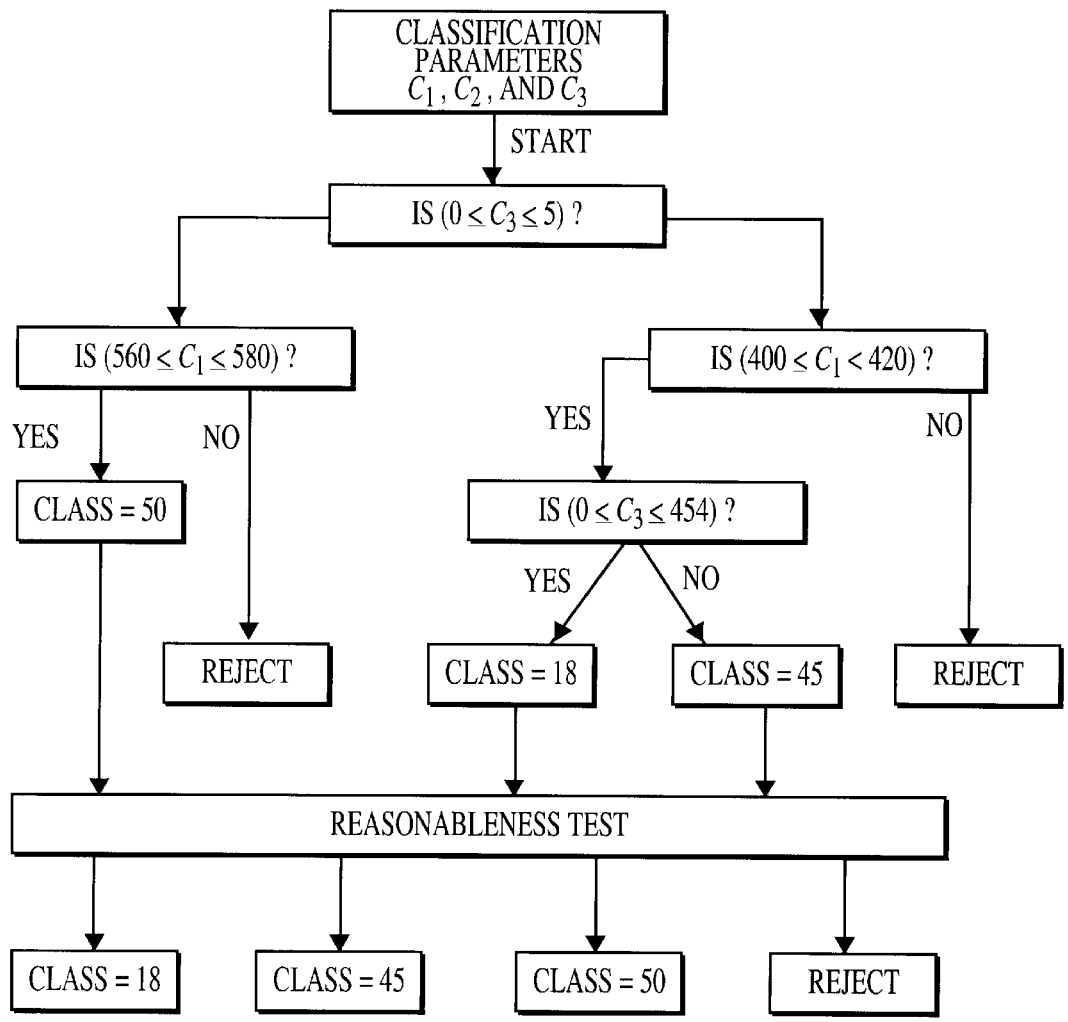
FIG. 14 shows a decision tree view for an illustrative (experimental example) discriminant table.

The absence of fluorescence ($C_2$ and $C_3$) immediately discriminates the clear beads (subset 50) from beads in the other two subsets. Subsets 45 and 50 were further discriminated by side light scatter ($C_1$) and red fluorescence ($C_3$). Linear discriminant functions based on these observations and created as described in Section 6.2(c); are shown in FIG. 13c. Accepting only clear beads with side light scatter ($C_1$) within ±0.25 standard deviations of the mean, doublets (two beads stuck together) were eliminated from the analyses. The remaining beads were classified by red fluorescence ($C_3$) at a midpoint of 59.6. A decision tree based on the discriminant function table (FIG. 13c) is shown in FIG. 14.

In this experiment, each of four samples (e.g., blood serum from four patients) contained all three antigen-microsphere complexes and either 1 or 2 different fluorescent antibodies in PBS buffer. After addition of the antibodies, the reactions were incubated at room temperature for 45 minutes, and then analyzed on the "FACSCAN" using side light scatter ($C_1$), orange fluorescence ($C_2$), and red fluorescence ($C_3$) as classification parameters. Green fluorescence was used as the measurement parameter ($F_m$); an increase in green fluorescence by 30-fold indicates a specific interaction between an antigen and its corresponding fluorescinated antibody. In other words, if a subset's mean measured $F_m$ value is greater than 30-fold times that subset's baseline $F_m$ value, then the target analyte is determined to be present. These "interpretive" observations are embodied in the interpretation table shown in FIG. 13d.

Once the assay database was built, it was tested by running 5,000 beads from each bead subset individually through the system. After rejecting 23.8% of the beads as doublets, the remaining crimson beads (subset 18) were classified with 99.88% accuracy. Dark red beads (subset 45) were classified with 99.96% accuracy with 22.9% rejected as doublets. Clear beads (subset 50) were classified with 100% accuracy with 9.4% of the beads rejected as doublets.

The three bead subsets were pooled to form an assay beadset and divided into 4 sample tubes and processed by the system shown in FIG. 1. The contents of each sample and the mean measured fluorescence ($F_m$) for each bead subset are listed in FIG. 13e. The inventive method correctly identified the antibody or antibodies present in each sample.

An Experimental Refinement

In an alternative embodiment using a $C_4$ (e.g., orange fluorescence) labeled reactant as a classification parameter, a variety (for example five) of protein antigens are employed. Bead subsets are first generated based on differences in one or more of $C_1$, $C_2$, and $C_3$. Next a selected antigen labeled with Cy3NHS (an orange fluorophore) is bound to the beads in each subset. To minimize the measured orange fluorescence coefficient of variation for each bead subset, the beads are sorted with a high speed cell sorter so that only a narrow range of antigen (orange fluorophore) is found on each bead within a subset. Care should be taken to select or prepare the beadset so that different $C_4$ values are measured/obtained for each of the (e.g., five) different antigens used. In other words, the measured intensity of $C_4$ for AgA should differ from the measured intensity of $C_4$ from AgB, etc. To ensure that uniformity is achieved, saturation binding with fluoresceinated monoclonal antibody is tested—each bead ought to have restricted ranges of both orange and green fluorescence. While the construction of beadsets by this method is more laborious, the increase in measurement precision may be useful and will allow the sampling of fewer beads to arrive at a suitable determination of antibody concentration.

The assays previously mentioned measure any antibody with specificity for antigen upon an appropriately labeled bead. The antigen can be quite simple or rather complex and thus, the inventive methods can measure a highly restricted antibody or a broad array of antibodies. For example, a hexapeptide just large enough to bind to a monoclonal antibody can be employed as antigen or a large protein with many epitopes can be used. One of ordinary skill will recognize that the level of antibody eventually found associated with the bead ($F_{m1}$) is a function of the number of epitopes per bead, the concentration of epitopes, the amount of antibody and the affinity of the antibody and the valence of the antibody-antigen interaction.

6.4 Displacement Assays

Assays for many substances in a clinical laboratory are based on the interference with specific ligand-ligate or antigen-antibody interactions. In these assays, one member of the ligand-ligate pair is labeled with the $F_m$ fluorophore and one member is immobilized on the beads. Soluble, unlabeled material (analyte), which may be ligand or ligate, is added to the reaction mixture to competitively inhibit interaction of the labeled component with the immobilized component. It is usually not important which member of the pair is labeled and which is immobilized; however, in certain assays, functional advantages may dictate the orientation of the assay.

In an exemplary assay of this type, each bead subset is modified with an antigen. The antigen-coated beads are then reacted with an $F_m$ labeled antibody specific for the antigen on the bead surface. Subsequent addition of a test fluid containing soluble analyte (inhibitor) will displace the $F_m$ labeled antibody from the beads in direct proportion to the concentration of the soluble analyte. A standard curve of known analyte concentrations is used to provide accurate quantification of analyte in the test sample.

One of ordinary skill will recognize that the time necessary to achieve equilibrium may be quite lengthy due to the kinetics and association constant of the interaction. To lessen the time required for the assay, the fluid containing the beadset may be subjected to dissociating conditions such as a change in pH, ionic strength or temperature, after mixture of the beadset with the sample to be tested. Alternatively, the $F_m$ labeled component may be added to the beadset after addition of the test sample. In either case, it is not necessary for equilibrium to be achieved to determine analyte concentration if the kinetics and linearity of the assays have been established.

6.5 Nucleic Acid Measurement

The power and sensitivity of PCR has prompted its application to a wide variety of analytical problems in which detection of DNA or RNA sequences is required. One major difficulty with the PCR technique is the cumbersome nature of the methods of measuring the reaction's products—amplified DNA.

A major advance in this area is described in our co-pending application entitled "Methods and Compositions for Flow Cytometric Determination of DNA Sequences by R. Jerrold Fulton, filed on Oct. 11, 1995. That advance employs a flow cytometric bead-based hybridization assay which permits the extremely rapid and accurate detection of genetic sequences of interest. In a preferred embodiment of that invention, a bead to which a nucleic acid segment of interest has been coupled is provided. A PCR product of interest (or any other DNA or cDNA segment) is detected by virtue of its ability to competitively inhibit hybridization between the nucleic acid segment on the bead and a complementary fluorescent DNA probe. The method is so sensitive and precise as to allow the detection of single point mutations in the PCR product or DNA of interest. Although that method in itself provides a pivotal advance in the art of analyzing PCR reaction products, the further discovery of methods of multiplexing such an analysis, compounds the method's power and versatility to allow analysis of a number of DNA products in a single sample as described more fully below.

The multiplexed DNA analysis method described here can be applied to detect any PCR product or other DNA of interest for specific polymorphisms or mutations. With the multiplexed techniques provided by the instant invention, individuals can be screened for the presence of histocompatibility alleles associated with susceptibility to diseases, mutations associated with genetic diseases, autoimmune diseases, or mutations of oncogenes associated with neoplasia or risk of neoplasia. The analysis of DNA sequences occurs generally as follows:

1. A beadset containing subsets of beads coupled to nucleic acid sequences of interest is prepared by coupling a unique synthetic or purified DNA sequence to the beads within each subset.
2. Fluorescent probes complementary to the DNA coupled to each bead subset are prepared. Methods known: in the art, e.g., as described in U.S. Pat. No. 5,403,711, issued Apr. 4, 1995 and incorporated herein by reference, or other methods may be used to fluorescently label the DNA. Since each probe will bind optimally only to its complementary DNA-containing subset, under the conditions of the assay, the fluorescent probes may be added to the subsets before or after the subsets are pooled, and before or after addition of the DNA test sample(s) of interest.
3. Tissue, fluid or other material to be analyzed is obtained, and DNA is purified and/or amplified with PCR as necessary to generate the DNA products to be tested.
4. The DNA samples of interest are then mixed with the pooled beadset under suitable conditions to allow competitive hybridization between the fluorescent probes and the DNA of interest.
5. The beadset is then analyzed by flow cytometry to determine the reactivity of each bead subset with the DNA sample(s). If the test sample contains a DNA sequence complementary to the DNA of a given bead subset then that subset will exhibit a decreased $F_m$ value relative to the $F_m$ value of beads to which a control DNA has been added. A computer executed method in accordance with the current invention can determine the subset from which each bead is derived, and therefore, the identity of the DNA sequence on the bead and any change in $F_m$.

6.5(a) Detection of Foreign DNA

The methods of the present invention find wide utility in the detection of foreign DNA's in, for example, diagnostic assays. Although the DNA segment to be analyzed can be any DNA sequence, in accordance with this embodiment the selected segment will be a DNA segment of a pathogenic organism such as, but not limited to, bacterial, viral, fungal, mycoplasmal, rickettsial, chlamydial, or protozoal pathogens. The procedure has particular value in detecting infection by pathogens that are latent in the host, found in small amounts, do not induce inflammatory or immune responses, or are difficult or cumbersome to cultivate in the laboratory. The multiplexed DNA detection method of the present invention is likely to find particular utility as a diagnostic assay for analysis of a sample from a patient having clinical symptoms known to be caused by a variety of organisms using a beadset designed to detect DNAs from the variety of organisms known to cause such symptoms to determine which of such organisms is responsible for the symptoms. DNA would be extracted from tissue, fluid or other sources and analyzed as described above.

6.5(b) Analysis of Genetic Polymorphisms

The invention may also be used to measure a variety of genetic polymorphisms in a target DNA of interest. For example, there are several genes in the MHC and many are polymorphic. There are at least two applications in which determination of the alleles at each position of the MHC is of critical importance. The first is the determination of haplotype for transplantation, and the second is determination of haplotype as indicator of susceptibility to disease. See Gross et al., "The Major Histocompatibility Complex-Specific Prolongation of Murine Skin and Cardiac Allograft Survival After In Vivo Depletion of $V\beta^+T$ Cells," J. Exp. Med., 177, 35–44 (1993). The MHC complex contains two kinds of polymorphic molecules, Class I genes, HLA A, B and D which have 41, 61 and 18 known alleles and Class 10 genes, HLA-DRI,3,4,5 HLA-DQAI and BI HLA-DP, DPA1, DPB1, also with many alleles. Each human can have up to 6 co-dominant Class I genes and 12 co-dominant Class 10 genes.

In the case of transplantation, the closer the match between the donor and recipient the greater the chance of transplant acceptance. A multiplexed assay in accordance with the invention may be employed to perform tissue typing quickly and accurately to identify suitable matches for transplantation.

In the situation of disease association, it has been found that individuals bearing certain alleles are more prone to some diseases than the remainder of the population. The frequency of alleles of the MHC genes is not equal, and sets of alleles are frequently found (linkage disequilibrium) so that the identification of the exact set of alleles associated with many diseases is feasible. As one example, insulin-dependent diabetes mellitus (IDDM) is associated with certain HLA-DQ alleles. The number of alleles of DQ in the population is modest and genetic typing by PCR amplification and hybridization with allele specific probes has been shown to be practical. See Saiki et al., "Genetic Analysis of Amplified DNA with Immobilized Sequence-Specific Oligonucleotide Probes," PNAS USA, 86, 6230–6234 (1989).

For an assay of MHC in accordance with the invention, DNA is obtained from blood or other extractable source, and amplified with primers specific for the MHC genes under analysis, for example, HLA-DQA. For a full genotyping of the MHC, several samples of DNA would be amplified with different sets of primers to accommodate the large number of loci and the high degree of polymorphism. The PCR products are then screened for specific alleles using beadsets and fluorescent probes as described above.

6.5(c) Mutation Analysis of Selected Genes: Screening Procedures

There are several methodologies for determining and comparing DNA sequences in order to detect mutations which are associated with disease or neoplasia. When adapted to a bead-based, multiplexed format in accordance with the current invention, hybridization analysis allows for the rapid screening of multiple genetic loci for multiple wild type and mutant sequences.

In a preferred embodiment of the invention, a given genetic locus, or multiple loci, can be simultaneously screened for the presence of wild type or mutant sequences. In the same analysis, multiple known mutations can be distinguished from each other and from the wild type sequence and uncharacterized mutations. In addition, the homozygosity or heterozygosity of known sequences can be determined.

A general approach for detecting a DNA mutation in accordance with this aspect of the invention is as follows. In a first step, a suitable probe for detecting a mutation of interest is selected. In an illustrative embodiment, selected oligonucleotides, representing wild-type and mutant sequences, from a region of a gene known to contain a mutation are prepared. Such oligonucleotides are coupled to microspheres by techniques known in the art, (e.g., carbodiimide coupling, or other means) to produce individual aliquots of beads having known oligonucleotides coupled thereto. The oligonucleotides must be a sufficient length to allow specific hybridization in the assay, e.g., generally between about 10 and 50 nucleotides, more preferably between about 20 and 30 nucleotides in length. In a preferred embodiment, a saturating amount of the oligonucleotide is bound to the bead. Fluorescent oligonucleotides, complementary to all or part of the sequences attached to each bead, are also prepared.

Next, PCR primers are selected to amplify that region of the test DNA corresponding to the selected probe, which are then used to amplify the particular region of DNA in the sample that contains the sequence corresponding to the oligonucleotide coupled to the beads. Either double stranded or single stranded PCR techniques may be used. If double stranded product is produced, the amplified PCR product is made single stranded by heating to a sufficient temperature to and for a sufficient time to denature the DNA (e.g., for about 1 to about 5 minutes at about 90–95° C. in 2.3×SSC hybridization buffer). The mixture is cooled, and the beads are added and incubated with the PCR product under conditions suitable to allow hybridization to occur between the oligonucleotide on the beads and the PCR product (e.g., at room temperature for about 10 minutes). The fluorescent DNA probe may then be added and the entire mixture incubated under hybridization conditions suitable to allow competitive hybridization to occur (e.g., 5 minutes at 65° C., then cooling to room temperature over a period of several hours in 2.3×SSC buffer). As those of skill in the art will recognize, the concentrations of the PCR product and fluorescent probe to be used may vary and may be adjusted to optimize the reaction.

In general, the concentrations of PCR product and fluorescent probe to be used are adjusted so as to optimize the detectable loss of fluorescence resulting from competitive inhibition without sacrificing the ability of the assay to discriminate between perfect complementarity and one or more nucleotide mismatches. In an exemplary assay, the concentration of PCR product complementary to the oligonucleotide bound to the beads may be on the order of 1 to 10 times the concentration of fluorescent probe used. If the PCR product is much longer than the bead bound oligonucleotide, the amount of PCR product may be increased accordingly to reflect relative molar concentrations in the region of DNA complementary to bead bound oligonucleotide. The fluorescent, probe should preferably be added in an amount sufficient to saturate the complementary oligonucleotide on the beads, e.g., in the range of from 1 to 1000 fold and more preferably 2–100 fold or 20–50 fold the concentration of oligonucleotide bound to the bead.

In a multiplexed assay employing the above principles, beadsets are seperably prepared, pooled, and the bead-based hybridization analysis performed. In order to screen a given locus for mutations, beadset subsets are prepared such that subset 1 is coupled to a DNA segment identical to the wild type sequence, subset 2 is coupled to a DNA segment identical to a known mutation 1 (which may represent a single or multiple point mutations, deletions or insertions), subset 3 is coupled to a DNA segment identical to a second known mutation 2, and so on. The subsets are then mixed to create a pooled beadset.

When PCR amplified DNA is analyzed with such a beadset, only the bead subsets containing sequences identical to the amplified sequences will show a decrease in fluorescence ($F_m$). A decrease in the $F_m$ of only subset 1 would indicate homozygous wild type; a decrease in the $F_m$ of both subset 1 and subset 2 would indicate heterozygous wild type and mutant 1, and so on. If the PCR product is less inhibitory than the known homozygous wild type, but does not preferentially hybridize with a known mutant subset, a new uncharacterized mutation is suggested. The PCR product could then be sequenced to characterize the mutation, and this information could be used to construct a new subset for the beadset to detect the newly discovered mutation.

6.6 Measuring Enzymes with Bead-Based Assays

Figure 15A:
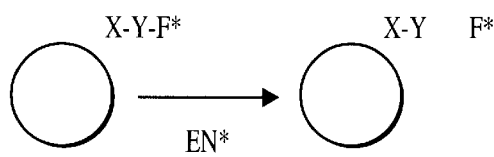
FIG. 15 shows the results of an exemplary multiplexed assay according to the invention.
Figure 15C:
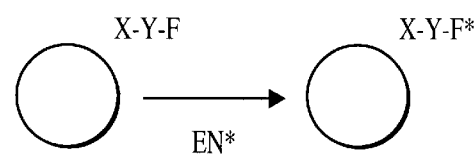
Figure 15B:
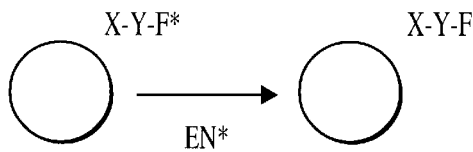

The invention may also be used in several formats for measurement of enzymes, enzyme inhibitors and other analytes. For example, bead subsets can be generated that are modified with selected fluorescent substrates which can be enzymatically cleaved from the bead, resulting in a loss of fluorescence ($F_m$). Enzymes that can be detected and measured using the invention include but are not restricted to, protease, glycosidase, nucleotidase, and oxidoreductase. Any enzyme that results in selected bond cleavage can be measured. A cartoon of the action of enzyme on a bead-bound enzyme is shown in FIG. 15a. An enzyme that acts upon a bead-bound substrate so that the bead-bound substrate becomes fluorescent or loses fluorescence comprises an assay for the level of enzyme affecting such a change. FIGS. 15b and 15c depict these situations. Alteration of the substrate could be an oxidation or reduction, alteration of a chemical bond such a hydrolysis or other alteration of the bead-bound substrate so that the fluorescence of the substrate is altered in intensity or spectrum.

Figure 15D:
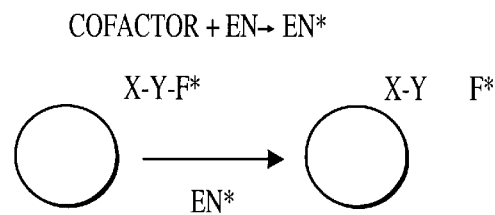

Enzymes that act upon pro-enzymes (convertases) can be measured using a bead-bound substrate providing the reaction mixture contains the pro-enzyme and beads bearing a substrate that can be acted upon by the active form of the enzyme. (Providing the specificity of each activated enzyme is distinct, a multiplexed assay is achievable in which several pro-enzymes can be measured at the same time.) The sample is introduced into a mixture of pro-enzymes under reaction conditions. After a fixed time interval during which the convertase acts upon the pro-enzyme, the beadsets specific for each enzyme generated from each pro-enzyme are added and the newly generated activities measured in a subsequent time period which is terminated when the beadsets are analyzed by flow cytometry. Such a process for a single pro-enzyme to enzyme conversion is illustrated by the cartoon in FIG. 15d.

The action of the enzyme can be measured in an indirect but facile manner using a bead bound substrate as depicted in FIG. 15e. The action of the enzyme on the bead-bound substrate results in the formation or revelation of a ligate for a fluorescent ligand present in the reaction mixture. The bead bearing the modified substrate then becomes fluorescent by virtue of binding of the fluorescent ligand to the newly formed ligate. In practice, the enzyme(s) would be added to the beadset under reactive conditions. After a defined time period during which the enzyme acts upon the bead bound substrate, the enzyme action would be stopped and the fluorescent ligands added and after a period for association of ligand with the beadsets, the mixture analyzed by flow cytometry. The fluorescent ligands could be of a single reactivity or multiple ligands employed, the critical specificity is that of the enzyme for the substrate.

The bead-bound substrate may be used to detect the activation of enzyme when the enzyme requires a cofactor for activity. Under this circumstance, the level of the cofactor becomes the limiting component of the reaction mixture and determination of the level of cofactor can be measured. Such a configuration is illustrated in FIG. 15f. The reaction mixture contains the bead-bound substrate as well as the apo-enzyme. After introduction of the analyte (enzyme cofactor), the reaction mixture is held under reactive conditions for a fixed period of time followed by analysis of the beads by flow cytometry, the level of cofactor limits the level of enzyme activity. Providing the enzymes present require different cofactors and have action on different substrate-bearing beadsets, several cofactors could be measured in a single assay mixture.

In short, bead-borne substrates can be used as reagent as are soluble substrates for enzymes. However, because each type of bead bearing a unique substrate can be distinguished, a mixture of bead subsets can be used to measure several enzyme activities simultaneously in the same reaction mixture.

Fluids that can be analyzed using these techniques include plasma, serum, tears, mucus, saliva, urine, pleural fluid, spinal fluid and gastric fluid, sweat, semen, vaginal secretions, fluid from ulcers and other surface eruptions, blisters, and abscesses, and extracts of tissues including biopsies of normal, malignant, and suspect tissues. An assay according to this aspect of the invention proceeds as follows:

1. Beads containing reactive surface groups (one of the following: amino, aldehyde, acid chloride, amidine, phenolic hydroxyl, phenyl amine, carboxyl) are obtained that can be discriminated on the basis of, for example, forward angle light scatter, $C_1$, right angle light scatter, $C_2$, and one of several wavelengths of fluorescence $C_3 \ldots C_n$ which are designated as orange and red fluorescence, for example, and comprise a number of subsets.
2. Subsets thus obtained are derivatized with a peptide (substrate) having a terminal fluorescent green group, for example fluorescein ($F_m$).
3. Unreacted surface groups and hydrophobic surface of the bead are blocked and the subsets are processed by a particle analyzer and sorter (FACSCAN) and a uniform population of particles are separated which have a low coefficient of variance for $F_m$. (e.g., 3%).
4. A fluid to be tested is diluted with an appropriate buffer and added to the beadset mixture to allow enzymes present in the sample to react with (cleave) their corresponding substrate on the surfaces of the beads.
5. After a defined period of time, the reaction is stopped and the entire mixture processed by a flow cytometer and results are determined.

The presence of an enzyme in the clinical sample is indicated by loss of fluorescence resulting from the cleavage of the fluorescent $F_m$ substrate from the bead surface. Because the beads are analyzed in a very small volume (e.g., about 6 picoliters) as they are passed through the flow cytometer's laser beam, interference from free fluorescent molecules (cleaved substrate) will not significantly interfere with the assay. This obviates the requirement of washing of the beads prior to assay and simplifies the procedure significantly.

Time

Time measurement is an important feature of the analysis. The essence of the measurement of an enzyme activity is a change in substrate with time. The activity can be determined by setting a period of time during which the clinical sample is in contact with the beads using standard conditions of pH, ionic composition and temperature. Two alternative processes are available for determination of the bead-bound substrate with time, that is the time expired while the enzyme(s) is (are) acting on each beadset(s).

External Time

In this configuration, as each bead is measured by the flow cytometer, the time at which each measurement was obtained is recorded along with the bead's other measurements. Prior to the beginning of the assay, the baseline measurement is determined. Once the enzyme (clinical sample) is added to the bead mixture, the sample analysis begins. As the beads proceed through the instrument, the time data collected is used to determine the length of time that the bead has been exposed to the clinical sample. The $F_m$ data collected over the period of the assay is used to determine the rate of change of substrate on the beads (kinetics) and thus the rate readily derived for each bead subset in the mixture exposed to the clinical sample.

Internal Time

Time can be determined and at the same time a quality control internally generated by including a "timer" bead subset that bears a substrate which is acted on by an enzyme that does not naturally occur in the clinical sample to be tested. The use of non-pathogenic microbial enzymes and substrates with human samples, for example, would suffice. The corresponding "timer" enzyme is added to the dilution buffer so that a known concentration of the "timer" enzyme is present in the buffer. The degree of action of the "timer" enzyme upon the beads in the "timer" subset can be measured as a function of the loss of fluorescence of the beads in the subset to ensure that proper reaction conditions are achieved. The level of fluorescence of the timer beads can thus be used as an internal standard and an estimation of time.

Determination of Enzyme Inhibitors or Regulators

In addition to direct assay of enzymes, an assay of this type may also be used to detect enzyme inhibitors or regulators. In accordance with this variation, samples being tested for inhibitors are added to the beadset followed by the corresponding enzymes. If inhibitors are present, the measured fluorescent ($F_m$) values will not be decreased to the same extent as a control containing no inhibitors. In accordance with FIG. 15, in a similar manner, inhibitors of enzyme activators or binders of cofactors can be measured.

As is seen, the present invention provides numerous advantages and overcomes many problems associated with prior art techniques of multiplexed diagnostic and genetic analysis apparatus and methods. It will be appreciated by those of ordinary skill having the benefit of this disclosure that numerous variations from the foregoing illustration will be possible without departing from the inventive concept described herein. Accordingly, it is the claims set forth below, and not merely the foregoing illustration, which are intended to define the exclusive rights claimed in this application program.

What is claimed is:

1. A particle set for flow analysis comprising:
   a pooled population of subsets of particles having the same size, the particles in each subset having (i) at least one characteristic classification parameter that distinguishes particles of one subset from those of another subset, the at least one characteristic classification parameter including at least one fluorescence emission intensity, (ii) a reactant specific for an analyte of interest, and (iii) a reactant surface-density specific for each subset of particles, wherein at least two subsets of particles are distinguishable from each other by their reactant surface-density.

2. The particle set according to claim 1, wherein said pooled population includes a plurality of subsets of particles per reactant.

3. The particle set according to claim 1, wherein said at least one characteristic classification parameter includes two distinct fluorescence emission intensities.

4. The particle set according to claim 1, wherein the at least one fluorescent emission intensity is obtained from one or more labels, which label the particles of each subset.

5. The particle set according to claim 4 in which the one or more labels comprise one or more fluorochromes.

6. The particle set according to claim 4 in which the one or more labels comprise one or more fluorophores.

7. The particle set according to claim 1, wherein said analyte of interest includes antigens, antibodies, peptides, proteins, nucleic acids, or enzymes.

8. The particle set according to claim 1, wherein said reactant includes a tracer antigen or antibody, a synthetic oligonucleotide, or a capture probe.

9. The particle set according to claim 1, wherein said reactant includes potentially interfering endogenous or exogenous substances.

10. The particle set according to claim 1, wherein the identity or density of said reactant present is selected to provide information relating to high-dose hook effects or dilutional linearity.

11. A population comprising a plurality of subsets of particles having the same size, the particles of one subset (i) being distinguishable from the particles of another subset and (ii) having one or more reactants of choice at a known surface-concentration or surface-density, which know surface-concentration or surface-density differs between the particles of one subset and the particles of another subset.

12. The population of claim 11 in which the one or more reactants of choice comprise a reactant specific for an analyte of interest.

13. The population of claim 12 in which the analyte of interest includes antigens, antibodies, peptides, proteins, nucleic acids, or enzymes.

14. The population of claim 11 in which the one or more reactants of choice comprise an analyte of interest.

15. The population of claim 14 in which the one or more reactants of choice are labeled with an antibody bearing a fluorescent dye.

16. The population of claim 2 in which the particles of each subset include two distinct fluorescence emission intensities.

17. The population of claim 16 in which the distinct fluorescence emission intensities are obtained from labels, which label the particles of each subset.

18. The population of claim 17 in which the labels comprise fluorochromes.

19. The population of claim 17 in which the labels comprise fluorophores.

20. The population of claim 11 in which the one or more reactants include a tracer antigen or antibody, a synthetic oligonucleotide, or a capture probe.

21. The population of claim 11 in which the one or more reactants include potentially interfering endogenous or exogenous substances.

22. The population of claim 11 in which the identity or density of the one or more reactants present are selected to provide information relating to high-dose hook effects or dilutional linearity.

23. A population comprising a plurality of subsets of particles having the same size, the particles of one subset (i) being distinguishable from the particles of another subset by the presence of one or more labels and (ii) having one or more reactants of choice at a known surface-concentration or surface-density, which know surface-concentration or surface-density differs between the particles of one subset and the particles of another subset.

* * * * *

UNITED STATES PATENT AND TRADEMARK OFFICE
CERTIFICATE OF CORRECTION

PATENT NO.    : 6,542,793 B1
DATED         : February 25, 2003
INVENTOR(S)   : Chandler et al.

It is certified that error appears in the above-identified patent and that said Letters Patent is hereby corrected as shown below:

Column 28,
Lines 17-18, claim 14 which reads:
"The population of claim 11 in which the one or more reactants of choice comprise an analyte of interest."
should read -- The population claim 11 is which the one or more reactants of choice comprise a substance that forms a complex with an analyte of interest. --

Signed and Sealed this

Twenty-third Day of December, 2003

JAMES E. ROGAN
*Director of the United States Patent and Trademark Office*